US010155085B2

(12) United States Patent
Gescheit et al.

(10) Patent No.: US 10,155,085 B2
(45) Date of Patent: Dec. 18, 2018

(54) THERAPEUTIC SYSTEM WITH AN ADAPTOR FOR AN INFUSION SET

(71) Applicant: Roche Diagnostics Operations, Inc., Indianapolis, IN (US)

(72) Inventors: Illai J. Gescheit, Tel Aviv (IL); Avraham Neta, Gilon (IL); Ofer Yodfat, Modi'in (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 714 days.

(21) Appl. No.: 14/624,744

(22) Filed: Feb. 18, 2015

(65) Prior Publication Data
US 2015/0157788 A1 Jun. 11, 2015

Related U.S. Application Data

(63) Continuation of application No. PCT/EP2012/066187, filed on Aug. 20, 2012.

(51) Int. Cl.
*A61M 39/10* (2006.01)
*A61M 5/14* (2006.01)
(Continued)

(52) U.S. Cl.
CPC .... *A61M 5/16804* (2013.01); *A61M 5/14244* (2013.01); *A61M 5/14248* (2013.01);
(Continued)

(58) Field of Classification Search
CPC ......... A61M 5/16804; A61M 5/14244; A61M 5/14248; A61M 2005/14252;
(Continued)

(56) References Cited

U.S. PATENT DOCUMENTS

2001/0034502 A1* 10/2001 Moberg .............. A61M 5/1456
604/154
2002/0173769 A1* 11/2002 Gray .................. A61M 5/1456
604/506
(Continued)

FOREIGN PATENT DOCUMENTS

WO 2008024810 A2 2/2008

*Primary Examiner* — Nathan R Price
*Assistant Examiner* — Courtney Fredrickson
(74) *Attorney, Agent, or Firm* — Dinsmore & Shohl, LLP

(57) ABSTRACT

A therapeutic system in an exemplary embodiment comprises a fluid delivery device having a fluid reservoir, an outlet port with a lumen for outputting fluid from the reservoir, a pump for pumping the fluid through the lumen and a controller for controlling the therapeutic system. The therapeutic system may also comprise an adaptor for an infusion set, the adaptor having a plug operable for attaching to the outlet port, and wherein the adaptor has an adaptor septum operable for being pierced by the lumen when attached to the outlet port. The therapeutic system comprises an infusion set recognition system, wherein the controller is operable to query the infusion set recognition system for infusion set data, wherein the infusion set data comprises an infusion set type, wherein the controller is operable to operate the pump to provide a basal dosage of the fluid if the infusion set type is not recognized.

24 Claims, 18 Drawing Sheets

(51) Int. Cl.
*A61M 5/168* (2006.01)
*A61M 5/142* (2006.01)
*G06F 19/00* (2018.01)
*A61M 5/158* (2006.01)

(52) U.S. Cl.
CPC ..... *A61M 39/1011* (2013.01); *G06F 19/3468* (2013.01); *A61M 39/10* (2013.01); *A61M 2005/14208* (2013.01); *A61M 2005/14268* (2013.01); *A61M 2005/1587* (2013.01); *A61M 2039/1072* (2013.01); *A61M 2205/52* (2013.01); *A61M 2205/6018* (2013.01); *A61M 2205/6027* (2013.01); *A61M 2205/6054* (2013.01); *A61M 2205/6072* (2013.01)

(58) Field of Classification Search
CPC ......... A61M 2005/14208; A61M 2005/14268; A61M 2005/1586; A61M 2005/1587; A61M 5/162; A61M 5/30; A61M 39/04; A61M 39/14
See application file for complete search history.

(56) References Cited

U.S. PATENT DOCUMENTS

| | | | | |
|---|---|---|---|---|
| 2006/0253086 A1* | 11/2006 | Moberg | .............. | A61M 5/1413 604/272 |
| 2008/0051738 A1* | 2/2008 | Griffin | ................ | A61M 5/1413 604/273 |
| 2010/0022988 A1* | 1/2010 | Wochner | ........... | A61M 5/14244 604/506 |
| 2010/0049164 A1* | 2/2010 | Estes | ................... | A61M 5/1413 604/504 |
| 2010/0298813 A1* | 11/2010 | Kudo | ...................... | A61M 5/14 604/524 |
| 2012/0215183 A1* | 8/2012 | Halili | ..................... | A61M 5/31 604/257 |

* cited by examiner

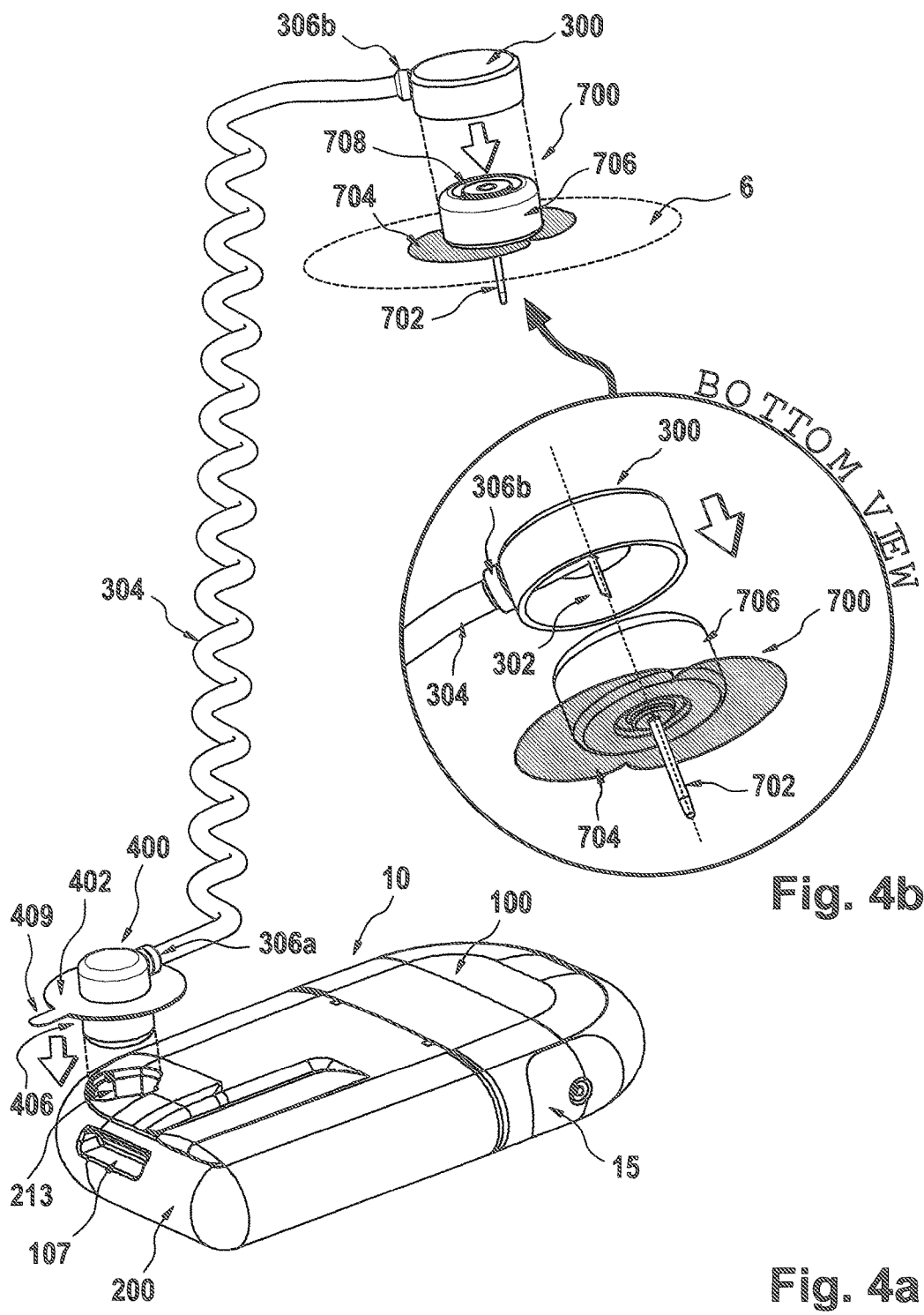

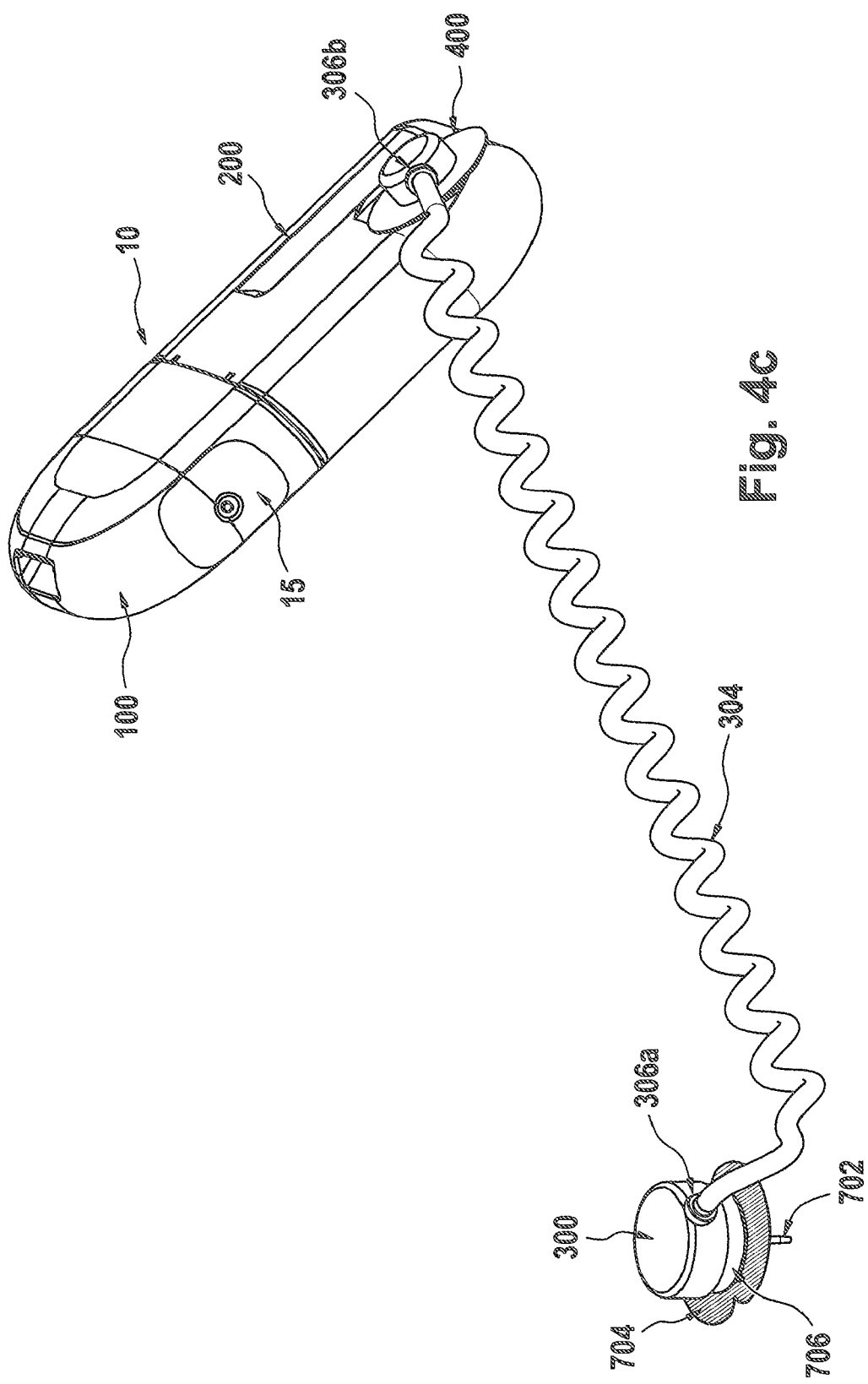

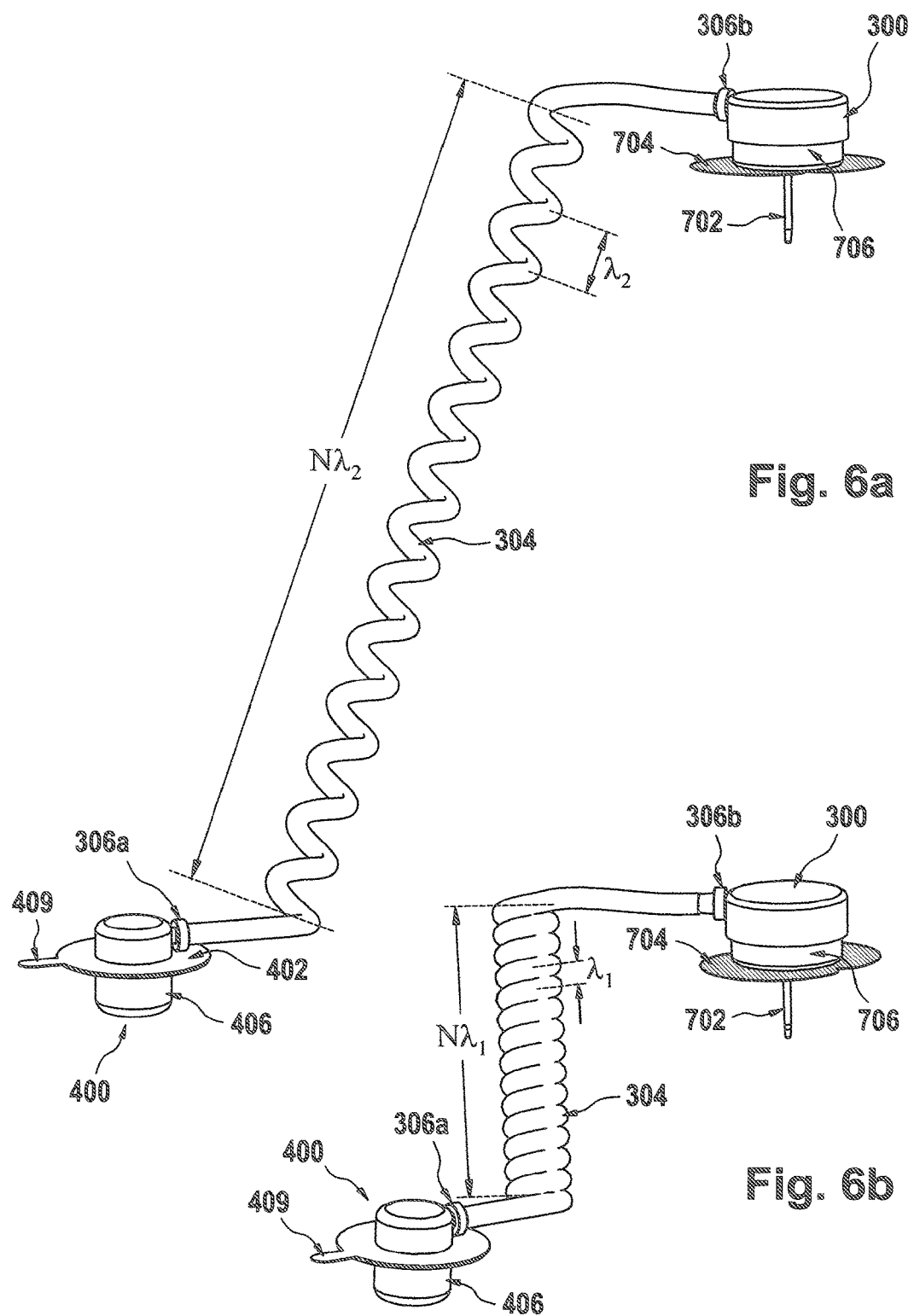

THERAPEUTIC SYSTEM WITH AN ADAPTOR FOR AN INFUSION SET

CROSS REFERENCE TO RELATED APPLICATIONS

The present application is a continuation application of and claims priority to PCT Patent Application No. PCT/EP2012/066187, filed Aug. 20, 2012, which is hereby incorporated by reference in its entirety.

TECHNICAL FIELD

The present disclosure relates to therapeutic systems for delivering fluid.

BACKGROUND

Therapeutic systems for delivering fluid may be used to dispense therapeutic agents or other liquids to a subject. An example of a therapeutic system is an insulin pump that is worn or adhered to a subject. Such pumps are typically worn in one of two fashions: as an external pump which supplies the liquid through an infusion set or where the pump is adhered to a surface of the subject.

These two types of therapeutic devices may be described as either "pager like" devices (i.e., conventional durable pumps), which administer insulin via infusions sets (having long delivery tubes), or patch devices, which their large surface adheres to the body of the subject. Typically the adherence location cannot be changed for about 3 days, unless the pump or cradle are discarded.

SUMMARY

According to at least one embodiment of the present disclosure, a therapeutic system and a kit are disclosed.

In at least one embodiment of the present disclosure, the therapeutic system comprises a fluid delivery device, wherein the fluid delivery device has: a fluid reservoir for storing a fluid; an outlet port with a lumen for outputting the fluid from the reservoir, wherein the outlet port is formed on an exterior surface of the fluid delivery device; a pump for pumping the fluid through the lumen; and a controller for controlling the therapeutic system, wherein the controller is operable for regulating the pumping of fluid through the lumen. Additionally, the exemplary therapeutic system comprises an adaptor for an infusion set, wherein the adaptor comprises a plug operable for attaching to the outlet port, and wherein the adaptor comprises an adaptor septum operable for being pierced by the lumen when attached to the outlet port. The therapeutic system optionally includes an infusion set recognition system, wherein the controller is further operable to query the infusion set recognition system for infusion set data, wherein the infusion set data comprises an infusion set type, wherein the controller is further operable to operate the pump to provide a basal dosage of the fluid if the infusion set type is not recognized.

In at least one embodiment of the therapeutic system, the adaptor is operable for supporting the fluid delivery device, wherein the adaptor and the fluid delivery device are operable for forming an interlocking connection for removably affixing the fluid delivery device to the adaptor. Further, the adaptor may comprise a tube mount operable for mounting a tube of the infusion set, wherein the tube mount has a first axis, wherein the plug has a second axis, wherein when the first axis and the second axis are projected onto a plane through the first axis the first axis and the second axis form an angle between 30 and 150 degrees.

In at least one embodiment of the present disclosure, a kit is disclosed which comprises a fluid delivery device, wherein the fluid delivery device comprises: a fluid reservoir for storing a fluid; an outlet port with a lumen for outputting the fluid; wherein the outlet port is formed on an exterior surface of the fluid delivery device; a pump for pumping the fluid through the lumen; a controller for controlling the therapeutic system, wherein the controller is operable to regulate the pumping of fluid through the lumen. The kit further comprising an adaptor for an infusion set, wherein the adaptor comprises a plug operable for attaching to the outlet port, wherein the outlet port comprises an adaptor septum operable for being pierced by the lumen. Additionally, the kit comprises a cradle for supporting the fluid delivery device, wherein the cradle and the fluid delivery device are operable for forming an interlocking connection for removably affixing the fluid delivery device to the cradle, wherein the cradle comprises an adhesive layer for attaching to an outer surface of a subject, wherein the cradle further comprises a mounting plug operable for attaching to the outlet port and for receiving a cannula with a cannula septum operable for being pierced by the lumen, wherein the kit enables the user to operate the fluid delivery device mounted on the outer surface of the subject or in an a remote mode where the fluid delivery device is connected to the infusion set.

BRIEF DESCRIPTION OF THE DRAWINGS

The drawings are not intended to be limiting in any way, and it is contemplated that various embodiments of the present disclosure may be carried out in a variety of other ways, including those not necessarily depicted in the drawings. The accompanying drawings incorporated in and forming a part of the specification illustrate several aspects of the present present disclosure, and together with the description serve to explain the principles of the present disclosure; it being understood, however, that this present disclosure is not limited to the precise arrangements shown.

FIGS. 4a, 4b, and 4c illustrate a fluid delivery device that can be disconnected from and reconnected to an infusion set, before and after connection of the fluid delivery device to the infusion set, according to at least one embodiment of the present disclosure.

FIG. 6a illustrates a stretched infusion set tube, according to at least one embodiment of the present disclosure.

FIG. 6b illustrates the infusions set tube of FIG. 6a in a compact configuration.

DETAILED DESCRIPTION

Figure 1A:
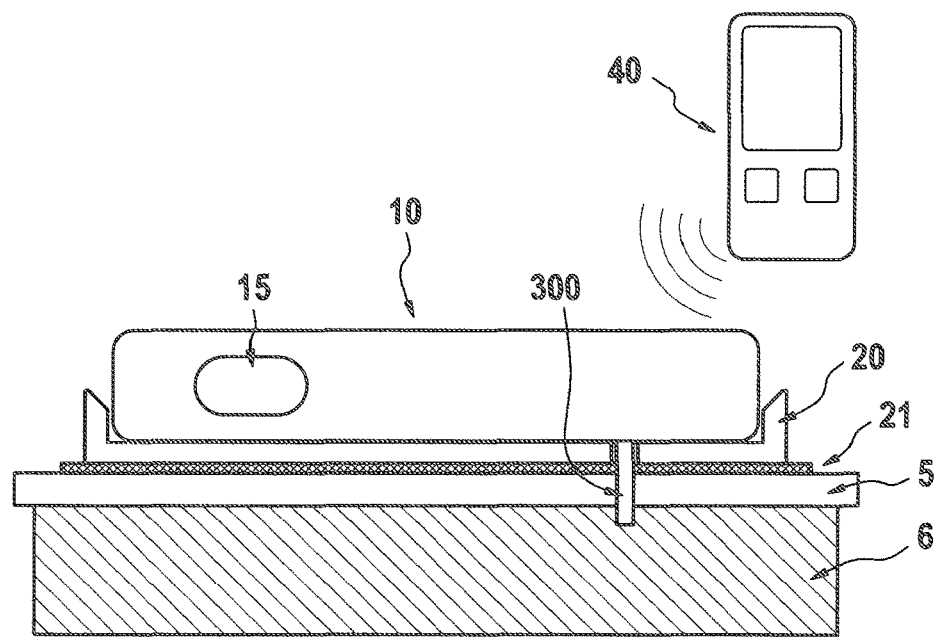
FIGS. 1a and 1b illustrate a therapeutic device, according to at least one embodiment of the present disclosure.

According to at least one embodiment of the present disclosure, a therapeutic system and kit are disclosed. Embodiments of the present disclosure provide a means of using a therapeutic device with an outlet port with a lumen with an infusion set. This may enable a so-called patch pump style therapeutic system to be used in the same fashion as a "pager like" therapeutic device. This may be achieved by using a plug which functions as an adaptor between the outlet port and an infusion set.

In some embodiments, the adapter may provide to the small, light weighted patch pumps, the ability to be connected to the subject's body in several ways, for example: via a cradle and an infusion set, interchangeably.

In some embodiments of the present disclosure, the adapter will make the therapeutic device more convenient to use since it provides a solution to all skin types by providing the patch pump with an infusion set having a relative small adhesion area. These embodiments of the present disclosure may have other advantages of the patch pump, such as being lightweight and having small dimensions.

In situations where a user may prefer to avoid the inconveniency of a large adhesion area, the adapter allows him/her to use an infusion set. In other situations, where the subject may prefer to conceal the pump, the adapter allows him/her to secure the pump to the body (by adhering the cradle/base). Thus, the adapter provides the user the ability to use a small patch pump both with its cradle and with an infusion set, interchangeably. Having this freedom with the same pump may also reduce the expenses of the user.

In at least one embodiment of the present disclosure, a therapeutic system is described which comprises a fluid delivery device. The fluid delivery device comprises a fluid reservoir for storing a fluid. The fluid may be a liquid. The fluid delivery device further comprises an outlet port with a lumen for outputting the fluid from the reservoir. The outlet port is formed on an exterior surface of the fluid delivery device. Essentially the output port is a location where the fluid can be pumped out of. The fluid delivery device may further comprise a pump for pumping the fluid through the lumen. The lumen may for example be a hollow needle. The fluid delivery device may further comprise a controller for controlling the therapeutic system. The controller is operable for regulating the pumping of fluid through the lumen.

A controller as used herein may encompass an electrical or mechanical apparatus operable for controlling or regulating the function of one or more devices or apparatuses. Examples of a controller include, but are not limited to: a microcontroller, a programmable logic controller, an embedded system, and a computer system. In some instances the controller may be programmable and have its function controlled by machine readable instructions.

In at least one embodiment, the controller is able to control the pump in order to regulate the fluid through the lumen. The therapeutic system may further comprise an adaptor for an infusion set. The adaptor comprises a plug operable for attaching to the outlet port. Further, the adaptor may also comprise an adaptor septum operable for being pierced by the lumen when attached to the outlet port. When the adaptor is placed into the outlet port the lumen is operable for piercing the adaptor septum. This embodiment may be advantageous because the use of the lumen and the adaptor septum may result in a system which reduces the amount of waste fluid when the adaptor is removed and then replaced into the outlet port. The lumen may in at least one embodiment be perpendicular to the exterior surface.

In at least one embodiment, the therapeutic system further comprises an infusion set recognition system. The controller of at least one embodiment of the fluid delivery device may be operable to query the infusion set recognition system for infusion set data. The infusion set data may comprise an infusion set type. Embodiments of the controller may be further operable to perform one or more of the following if the infusion set type is not recognized: disable operation of the pump and operate the pump to provide a basal dosage of the fluid.

In at least one embodiment, the infusion set recognition system may be any one of the following: an RFID system, a barcode reader, a hologram recognition system, and an electronic plug incorporated into the outlet port. Any one of these embodiments may be advantageous because they provide a means for the infusion set recognition system to positively identify the infusion set type and/or to retrieve infusion set data from the infusion set.

The infusion set recognition system, in at least one embodiment, has a specific mechanical arrangement, i.e. a mechanical coupling arrangement (e.g. snap-fit, particular assembly of specific shapes, catching system, bolt, lock, hasp, bibb or plug)

In at least one embodiment, the infusion set recognition system combines hardware and software arrangements. A mechanical fit then can condition further logical operations. For example, a barcode reader may only operate if a previous proper mechanical connection or coupling has been established.

In other words, the therapeutic system can comprise an infusion set recognition system which is any one of the following: an RFID system, a bar code reader, a hologram recognition system, an electronic plug incorporated into the outlet port, a mechanical coupling arrangement or a combination thereof.

In at least one embodiment, the therapeutic system further comprises an infusion set. The infusion set may be attached to the adaptor. The infusion set further comprises an information carrier for storing the infusion set data. The infusion set recognition system is adapted for retrieving the infusion set data from the information carrier by querying the infusion set. The information carrier in various embodiments may take different forms. For instance the information carrier may be a memory for storing machine readable memory such as a computer memory, optically encoded information such as a bar or other code, or it may be information retrieved electronically from something such as an RFID chip.

In at least one embodiment, the infusion set data may comprise any one of the following: sterility state, therapeutic system compatibility data or code, approved use data or code, lot number, batch number, hose diameter, manufacturer, approved therapy data or code, and combinations thereof.

In at least one embodiment, the infusion set recognition system is further operable for writing usage data to the information carrier. The usage data comprises any one of the following: prior use and cumulative use. The infusion set recognition system is further operable to query previously written usage data.

In at least one embodiment the controller is operable to disable and/or display a warning on a display in accordance with the previously written usage data. For instance if an infusion set has been used for too long or has been previously used there may be a display which the therapeutic system can control and then on which it displays a warning or message to the user.

In at least one embodiment the controller comprises a memory. The controller is operable for recording utilization data of the infusion set and the infusion set data in the memory.

In at least one embodiment, the therapeutic system is operable for sending the utilization data and the infusion set data to a computer system. The computer system may for instance be a server or data logger belonging to a company maintaining health records for the user or for a manufacturer of therapeutic systems. The utilization data may provide valuable information which may be used for monitoring the health state of the subject and/or for the reordering of supplies for use in conjunction with the therapeutic system. For instance the computer system could automatically order more fluid and/or infusion sets when the subject is in need of them.

In another embodiment the infusion set data further comprises a software update. The controller is operable for controlling the operation of the pump in accordance with the software update. This embodiment may be beneficial because the infusion set itself may contain machine readable instructions which enable the processor to properly control the pump to dispense the fluid through the infusion set.

In at least one embodiment the therapeutic system further comprises a cradle for supporting the fluid delivery device. The cradle and the fluid delivery device are operable for forming an interlocking connection for removably fixing the fluid device to the cradle. The cradle comprises an adhesive layer for attaching to the outer surface of a subject. The cradle further comprises a mounting plug operable for attaching to the outlet port and for receiving a cannula with a cannula septum operable for being pierced by the lumen when attached to the outlet port. In this embodiment the fluid delivery device is able to be mounted in the cradle which is able to attach to the outer surface of a subject. The infusion set would then allow the fluid to be delivered to the subject at a location other than where the fluid delivery device is. This embodiment may be beneficial because it enables a subject to wear the fluid delivery device however not at a point where the fluid is injected.

In at least one embodiment the adaptor is operable for supporting the fluid delivery device. The adaptor and the fluid delivery device are operable for forming an interlocking connection for removably affixing the fluid delivery device to the adaptor.

In at least one embodiment, the adaptor comprises an adhesive layer for attaching to the outer surface of a subject. Additionally, the adaptor may additionally comprise a clip operable for attaching the adaptor to a garment.

In at least one embodiment, the adaptor comprises a tube mount operable for mounting a tube of the infusion set. The tube mount has a first axis where the plug has a second axis. When the first axis and the second axis are projected onto a plane through the first axis and the first axis and the second axis form an angle between 30 and 150 degrees.

In at least one embodiment, the adaptor further comprises a tube mount operable for mounting to an infusion set tube. This embodiment may enable a user of the fluid delivery device to connect a variety of different infusion devices to it. The tube mount may be a Luer lock.

The therapeutic system may also comprise a set of tube adaptors operable for adapting infusion set tubes of different diameters to the tube mount. This embodiment may be beneficial because this enables the operator to use a larger variety of infusion sets with the fluid delivery device.

In at least one embodiment, the therapeutic system further comprises an infusion set attached to the adaptor. In some embodiments the infusion set may be permanently attached to the adaptor.

In at least one embodiment, the therapeutic system further comprises a tube with a first end and a second end. The first end is connected to the adaptor. The second end is connected to a tube port. The tube port adaptor further comprises a tube port septum. The therapeutic system further comprises a hub operable for attaching to the tube port. The hub comprises an adhesive layer for attaching to the outer surface of a subject. The hub comprises a hub cannula and a hub cannula septum. The hub cannula septum is operable for being pierced by the tube port lumen when the hub is attached to the tube port. In this embodiment the tube and the hub may function as an infusion set. The tube may conduct fluid from the fluid delivery device to the hub.

In at least one embodiment, the hub is further operable for attaching to the outlet port. The hub cannula septum is operable for being pierced by the lumen. This embodiment is advantageous because the hub may be used directly with the delivery device with or without the tube. Both the delivery device and the hub may be mounted directly on a subject. When the tube is used then the fluid delivery device may be remote to the hub.

In at least one embodiment, the therapeutic system further comprises an infusion set. The tube may be any one of the following: a spiral shape, is contained within a spring-loaded spool, has a convoluted shape, and is attached to an elastic strap.

In at least one embodiment, the outlet port further comprises a first electrical connector. The adaptor further comprises a second electrical connector operable for forming an electrical connection with the first electrical connector for transmitting a sensor signal to the processor. For instance there may be a sensor mounted at some point in the infusion set. In some embodiments the sensor may be an occlusion sensor and in other embodiments the sensor may be a sensor inserted into the subject. In still yet other embodiments there may be one occlusion sensor and/or one or more sensors inserted into the subject.

In at least one embodiment, the therapeutic system further comprises an infusion set. The infusion set comprises a sensor. The sensor in some embodiments may be connected through the first and second electrical connectors to the processor.

In another embodiment the sensor is an occlusion sensor or a flow sensor. The controller is further operable to receive the sensor signal from the sensor. The controller is further operable to detect an occlusion condition using the sensor signal. If the occlusion sensor returns a positive result that there is an occlusion or if the flow is reduced while the pump is pumping this may indicate an occlusion condition. The controller may also be further operable to generate a warning message if the occlusion condition is detected. This embodiment may be beneficial because it may prevent the pump from pumping fluid when there is an occlusion in the infusion set.

In at least one embodiment, the sensor is a subcutaneous sensor. The controller is further operable to receive the sensor signal. The controller is further operable to perform any one of the following: log the sensor signal and to adjust the pumping of the fluid through the lumen in accordance with the sensor signal. For instance the sensor could be a blood glucose sensor and the fluid may contain insulin. In this case on the basis of the blood glucose levels the level of insulin being supplied by the pump may be adjusted.

In at least one embodiment, the therapeutic system further comprises a network adaptor for communicating with a computer. The controller is further operable to identify an alert condition and to send an alert notification message to the computer using the network adaptor. The alert condition could be a condition of the fluid delivery device not functioning or it also may be an indication of a medical condition of a subject using the therapeutic system. The network adaptor may be, but is not limited to: a cellular telephone connection, a WIFI, or other network connection. Alerts may be sent to a server for further data management, for instance these may be sent to a doctor, a therapeutic system manufacturer or an insulin manufacturer.

In at least one embodiment, the fluid delivery device comprises a reasonable portion and a disposable portion. The reasonable portion comprises the pump, the memory, and the processor. The disposable portion comprises the fluid reservoir. In some embodiments a power source such as a battery may be included in the disposable portion and may also be disposable.

In at least one embodiment, the therapeutic system further comprises a support garment operable for supporting the fluid delivery device. This may be beneficial because it may make it more comfortable for a subject to wear or to carry the fluid delivery device.

In at least one embodiment, the fluid delivery system is an insulin pump.

In at least one embodiment, the present disclosure provides for a kit. The kit comprises a fluid delivery device. The fluid delivery device comprises a fluid reservoir for storing a fluid. The fluid delivery device further comprises an outlet port with a lumen for outputting the fluid. The outlet port is formed on an exterior surface of the fluid delivery device. The fluid delivery device further comprises a pump for pumping the fluid through the lumen. The fluid delivery device further comprises a controller for controlling the therapeutic system. The controller is operable to regulate the pumping of fluid through the lumen. The kit further comprises an adaptor for an infusion set. The adaptor comprises a plug operable for attaching to the outlet port. The outlet port comprises an adaptor septum operable for being pierced by the lumen. The kit further comprises a cradle for supporting the fluid delivery device. The cradle and the fluid delivery device are operable for forming an interlocking connection for removably fixing the fluid delivery device to the cradle. The cradle comprises an adhesive layer for attaching to the outer surface of a subject. The cradle further comprises a mounting plug operable for attaching to the outlet port and for receiving a cannula with a cannula septum operable for being pierced by the lumen. The kit enables the user to operate the fluid delivery device mounted on the surface of a subject or in a remote mode where the fluid delivery device is connected to an infusion set. Therefore, the subject in at least one embodiment would have the choice of using the cradle or the adaptor. In some embodiments the kit may include different types of cradles or more than one type of cradle. There may be a cradle which adheres to the user's skin and the user can connect and disconnect the pump from it. There may also be a cradle which is not adhered to the skin but is used as the adaptor to the infusion set.

In at least one embodiment, the cradle may operate interchangeably in a remote mode and a connected mode.

In at least one embodiment of the present disclosure, the infusion set includes a tube having a distal end and a proximal end, a pump connector, an infusion set body, and a subcutaneously insertable cannula (hereinafter "cannula"). The infusion set body is coupled to the subcutaneously insertable cannula and may be adhered to the skin of the subject. The tube's distal end can be coupled to the infusion set body and the tube's proximal end can be coupled to the pump connector. The pump connector is configured for connecting to the fluid delivery device, enabling fluid communication between a reservoir, of the fluid delivery device, and the infusion set. Thus, the infusion set enables fluid flow from the reservoir to the body of the subject, e.g., subcutaneous tissue, through the tube and the cannula. In some embodiments, a conventional infusion set can be used. In some embodiments, other infusion sets can be used, as disclosed, for example, in FIGS. 4-6.

The cradle may be configured as a base which fits the dimensions of the fluid delivery device, and configured for enabling removable connection of the fluid delivery device to the cradle. The cradle can be secured to the skin of the subject (e.g., via an adhesive), thus, the subject may connect and/or disconnect the fluid delivery device to and/or from the cradle at her/his discretion, while the cradle remains attached to the body. The cradle may be further configured for receiving a subcutaneous insertable cannula enabling fluid communication between the reservoir (of the fluid delivery device) and the body, without using a tube which is external to the body and/or to the fluid delivery device.

In some embodiments, a system which includes the fluid delivery device, the cradle and the infusion set may further include connectors and/or adapters enabling interchangeable use of the skin adherable cradle and/or the infusion set.

Figure 1B:
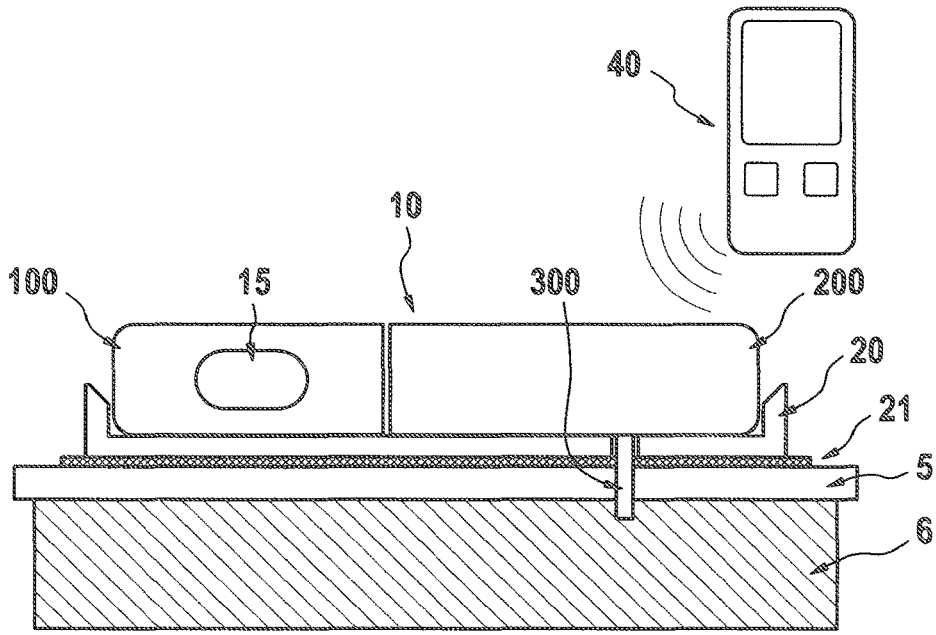

FIGS. 1a and 1b illustrate examples of a system or therapeutic device which includes a fluid delivery device 10 connectable to a cradle 20.

The fluid delivery device 10 may include a reservoir containing a fluid, e.g., insulin, and an outlet port provided with a connecting lumen configured to enable fluid communication between the reservoir and the subject's body, via a subcutaneously insertable cannula 300.

The cradle 20 may be configured for securing the fluid delivery device 10 to the body of the subject. For example, the cradle 20 may be adhered to the outer surface 5 of the subject via an adhesive layer 21 provided on a bottom surface of the cradle, and include one or more securing mechanisms, e.g., snaps or latches, to removebly secure the fluid delivery device 10 to the cradle 20. The cradle 20 may also contain a passageway for insertion of a cannula 300 into the body of the subject, to the subcutaneous tissue 6, for example.

In some embodiments, the system may further include a remote control (RC) 40 for at least controlling the fluid delivery device. In some embodiments, the remote control may be configured as a handheld device for programming fluid infusion rates, controlling the fluid delivery device, acquiring data, and providing visual, audible and/or vibratory notifications. In some embodiments, the RC may include an integrated blood glucose monitor. In some embodiments, the remote control may be configured, without limitation, as a wristwatch, a cellular phone, a personal digital assistance, a smartphone, a media player, or a personal computer. In some embodiments, the fluid delivery device 10 can be controlled, e.g., controlling bolus delivery, via buttons/switches 15 located on the fluid delivery device 10.

In some embodiments, the fluid delivery device, e.g., insulin pump, may further include an analyte, e.g., glucose, sensor providing an open and/or closed loop system.

The fluid delivery device 10 may be composed of a single part, see FIG. 1a, or of two parts, see FIG. 1b. The two-part device 10 illustrated in FIG. 1b may include a reusable part (RP) 100 and a disposable part (DP) 200. In some embodiments, the reusable part 100 may contain the relatively expensive components, e.g., processor, electronic components, and at least a portion of the driving mechanism, e.g., motor, one or more gears. The disposable part 200 may include the reservoir and the outlet port provided with the connecting lumen. In some embodiments, the disposable part 200 may also include a portion of the driving mechanism, e.g., drive screw. Buttons/switches 115 may be located on the reusable part 100. In some embodiments, the RP 100 may be a durable unit/assembly which is replaced, for example, every three months, and the DP 200 may be a single-use unit/assembly, which is discarded and replaced, for example, every 2-3 days. In other words, a single RP 100 may be coupled to approximately thirty or more different DPs 200 throughout its lifetime.

Figure 2A:
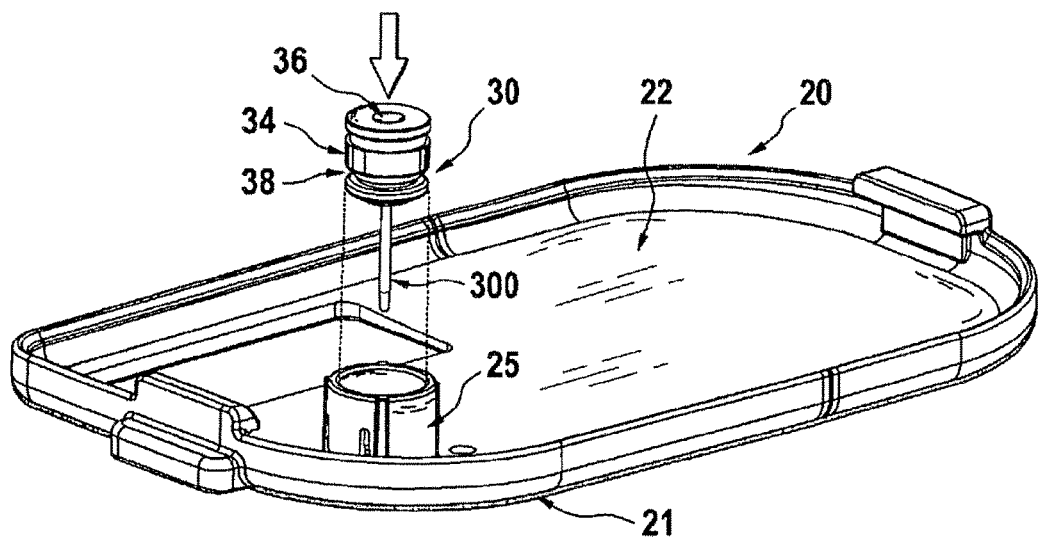
FIGS. 2a and 2b illustrate a cradle and a cannula cartridge, according to at least one embodiment of the present disclosure.
Figure 2B:
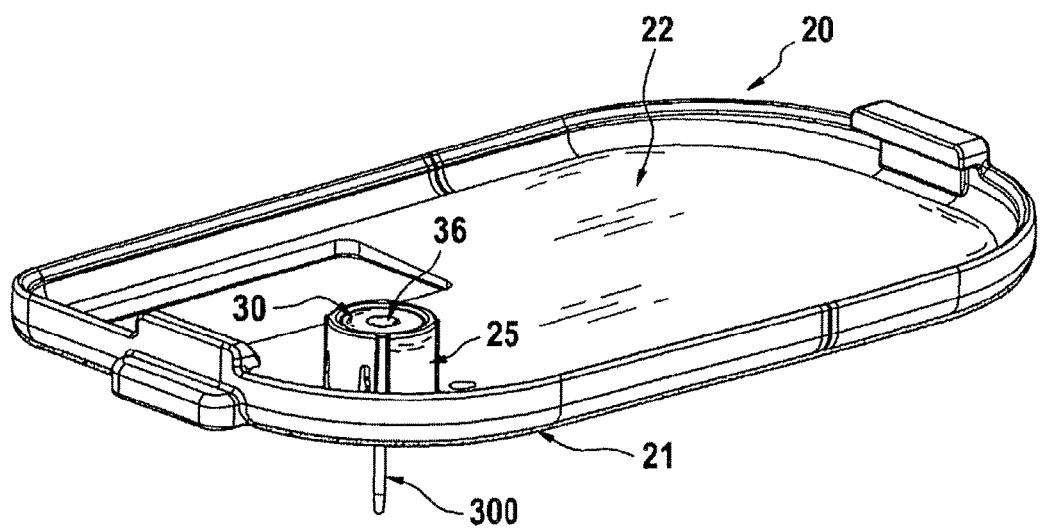

FIGS. 2a-b illustrate an example of a cradle 20 and a cannula cartridge 30. In some embodiments, the cradle 20 may be configured as a substantially flat sheet or plate including a surface that may be adhered the outside surface 5 of the subject, e.g., via an adhesive layer 21 provided on a bottom surface of the cradle. The cradle 20 may include a passageway 25 receiving the cannula cartridge 30. In some embodiments, the passageway 25 may be defined by a well structure configured as a protrusion, e.g., a tubular protrusion, emerging upwardly from the substantially flat sheet. In some embodiments, the cannula cartridge 30 includes a subcutaneously insertable cannula 300, e.g., a soft cannula made of Polytetrafluoroethylene, and a cannula hub 34 which may be attached to the cannula 300. The cannula hub 34 may include at least one recess, e.g., an annular recess 38, for receiving at least one corresponding anchoring mechanism, e.g., one or more latches, of passageway 25 and establishing a secure connection of the cannula cartridge 30 to the cradle, when the cannula 300 is inserted into the subject's body through the passageway 25 of the cradle. The cannula hub 34 may comprise a self-sealable septum 36 which may be pierced by a connecting lumen, provided in the fluid delivery device 10, for example. When not in use the self-sealable septum 36 may be covered by a protecting cap.

FIG. 2a illustrates cradle 20 and cannula cartridge 30 before connection and FIG. 2b illustrates cradle 20 and cannula cartridge 30 after connecting the cannula cartridge to the cradle via the passageway 25.

Figure 3:
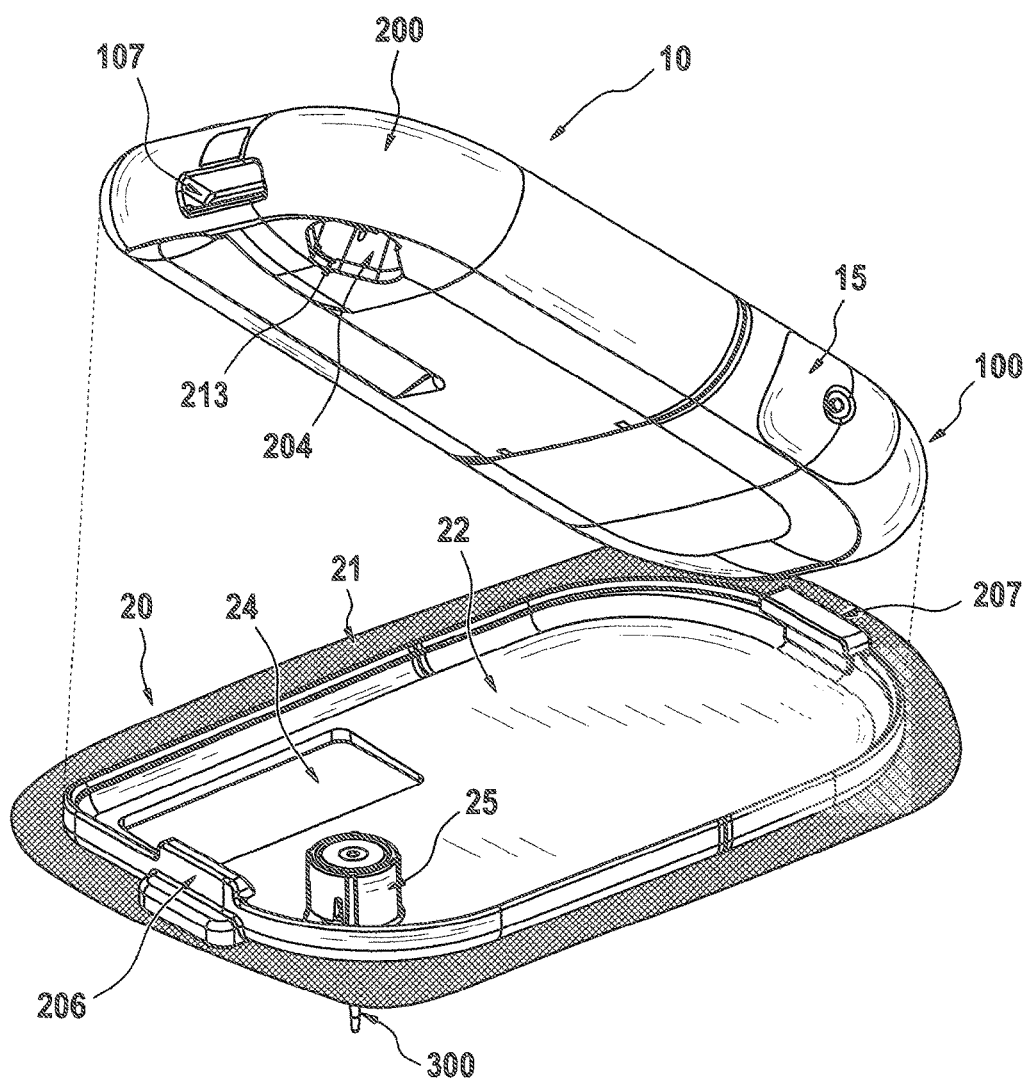
FIG. 3 illustrates a fluid delivery device that can be disconnected from and reconnected to a cradle, according to at least one embodiment of the present disclosure.

FIG. 3 illustrates an example of a fluid delivery device 10 that can be disconnected from and reconnected to a cradle 20, after insertion of a cannula 300 through passageway 25 of the cradle 20. The passageway 25 may be configured to fit outlet port 213 within the fluid delivery device 10. The outlet port 213 may be provided with a connecting lumen 204 configured to pierce a septum of the cannula, so that upon connection of the fluid delivery device 10 to the cradle 20, the outlet port 213 is fitted onto passageway 25 and the connecting lumen 204 enables fluid communication between the fluid delivery device 10 and the cannula 300. When not in use connecting lumen 204 may be covered by a protecting cap.

In some embodiments, the cradle 20 may include one or more securing mechanisms, e.g., snaps, latches, 206 and/or 207 to secure the fluid delivery device 10 to the cradle 20 after connection. The securing means 206 and/or 207 may be received within indentation 107 in the fluid delivery device 10. The securing means 206, 207 may be configured to enable the disconnection and the reconnection of the fluid delivery device 10 and the cradle 20 at the subject's discretion.

The cradle 20 may include a cradle base 22 fitted to the fluid delivery device 10. The cradle base 22 may comprise one or more openings, for example opening 24 which receive the reservoir, located in the delivery device 10. In some embodiments, the cradle 20 may be skin-adherable and include an adhesive layer 21 at its bottom. The adhesive layer footprint may be larger, equal or smaller than the cradle size.

In some embodiments the cradle 20 may be connected to an adapter configured to connect the cradle to an infusion set instead of to cannula 300. In some embodiments, while the delivery device 10 may be fitted on the cradle base 22 and onto passageway 25, the adapter may be connected to the bottom side of passageway 25, allowing fluid flow from the pump through the tube and the cannula of the infusion set into the body of the subject.

In some embodiments, the fluid delivery device 10 may be configured for releasably connecting to a plurality of devices, for example, to both the cradle 20 and an infusion set. For example, the fluid delivery device 10 may be connected to the cradle 20 via indention 107 provided on the fluid delivery device 10, as previously described, and/or, alternatively, to the infusion set via an adapter 400, coupled to outlet port 213, as illustrated in FIGS. 4a-c.

FIGS. 4a-4c illustrate an example of fluid delivery device 10 that can be disconnected from and reconnected to an infusion set, before and after connection of the fluid delivery device 10 to the infusion set.

In some embodiments, the fluid delivery device 10 may be configured as a single part device or a two part device, and may include at least some of the features as described with reference to FIGS. 1a-1b.

In some embodiments, the infusion set may include a tube 304 having a distal end and a proximal end and an infusion set body 700 coupleable to a subcutaneously insertable cannula 702.

The infusion set body 700 may include a hub 706 provided with a self-sealable septum 708. The hub 706 may be rigidly connected to the subcutaneously insertable cannula 702. The infusion set body 700 may also include an adhesive layer 704 for securing the infusion set body 700 to the outer surface of the subject.

In some embodiments, a conventional infusion set may be used. In other embodiments, the tube 304 and the infusion set body 700 may be detachable. For example, the tube's distal end can be coupled to the infusion set body 700 via adapter 300 attached to the tube by connector 306b. The adapter 300 may be configured to receive the hub 706. In some embodiments, as can be seen in FIG. 4b, which is a zoomed-in bottom view of the adapter. The adapter 300 may be provided with a connecting lumen 302 for repetitively piercing the self-sealable septum 708, enabling disconnection and reconnection of the tube 304 to the infusion set body 700. When not in use, the connecting lumen 302 and/or the self-sealable septum 708 may be covered by protecting caps, not shown.

In some embodiments, the infusion set body 700 may be a port unit accompanied with a cannula structure secured to the outer surface of the subject, a cannula structure may be, for example, the cannula cartridge 30 as described in reference to FIG. 2. The port unit may be configured to enable the subject/user to adhere a much smaller and less bulky item to the skin instead of securing the larger cradle unit 20. The port unit may be coupleable to a cradle unit, to a tube and/or directly to a fluid delivery device.

The tube's proximal end can be coupled to a pump connector 306a. The pump connector 306a may be configured for connecting to the fluid delivery device, enabling fluid communication between a reservoir, for example located in the fluid delivery device, and the infusion set. Thus, the infusion set enables fluid flow from the reservoir to the body of the subject, e.g., subcutaneous tissue, through the tube 304 and the cannula 702. In some embodiments delivery device 10 may be configured for connection to the pump connector 306a of infusion set via an adapter 400. The adapter 400 may be configured to be connected and disconnected to and from the fluid delivery device 10 such that an adapter hub 406 may be received within outlet port 213 of fluid delivery device 10. In some embodiments, the adapter 400 may include a grip portion 402 with a grip handle 409 for comfortable attaching to and detaching of the adapter 400 to and from the fluid delivery device 10, by the user.

Figure 5A:
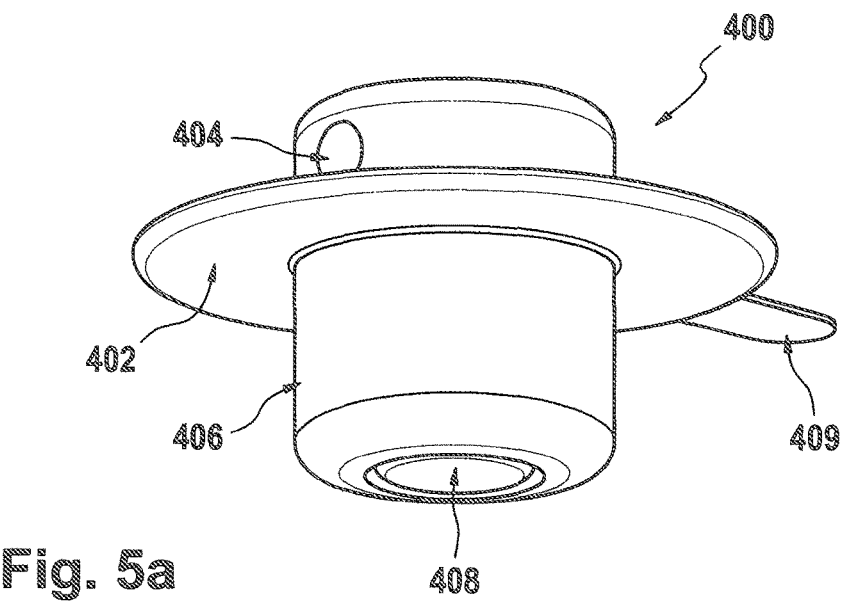
FIG. 5a illustrates an adapter configured for connecting the fluid delivery device, according to at least one embodiment of the present disclosure.

FIG. 5a illustrates an example of adapter 400 configured for connecting the fluid delivery device 10 and the infusion set. In some embodiments, the adapter 400 may comprise two connection sites, the first connection site may receive the fluid delivery device 10, and the second connection site may receive the tube 304 of the infusion set.

In some embodiments, the first connection site may include an adapter hub 406 configured, to be received within outlet port 213 of the delivery device. The adapter 400 may further include means for connection to the pump's outlet port, such as snaps, latches, and etc. at the first connection site. The adapter hub 406 may contain a self-sealable septum 408 configured to be pierced, for example, by a connecting lumen located within the outlet port, enabling repeated connection/disconnection of the adapter to and from the delivery device. The self-sealable septum 408 may have a proximal end and a distal end, the proximal end may contact the fluid delivery device 10 and the distal end may be coupled with a channel 407 within the adapter 400. The channel 407 may be configured for communicating fluid, infused from the fluid delivery device 10 to the tube 304, via the connecting lumen piercing the self-sealable septum 408. The channel 407 may further be configured to prevent fluid occlusion or leaks.

In some embodiments, the second connection site may include an aperture 404 configured for receiving the pump connector 306a located at the proximal end of the tube 304, enabling fluid communication between the channel 407 within the adapter and the tube 304.

Figure 5B:
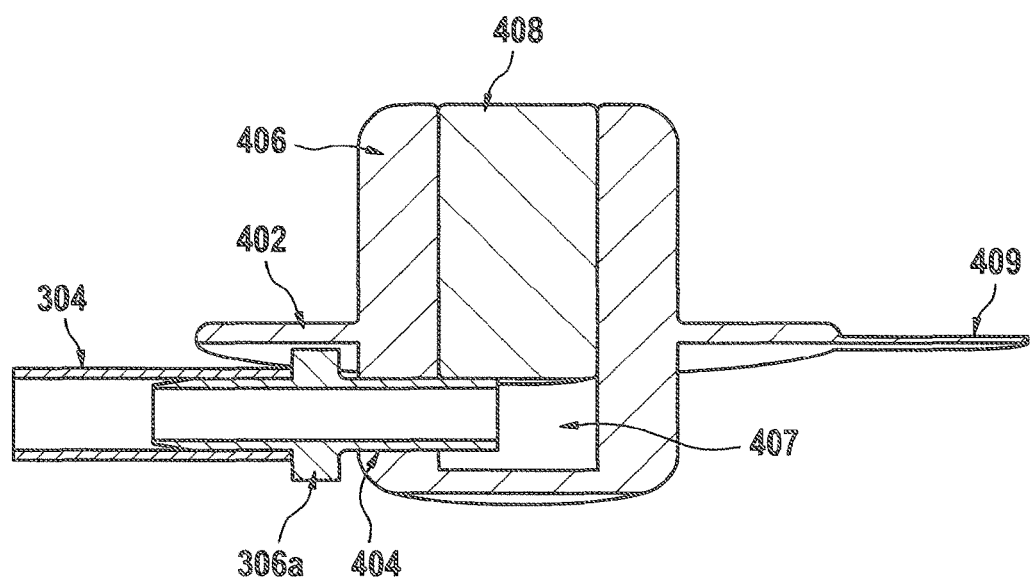
FIG. 5b illustrates a cross sectional view of an adaptor connected to a tube, according to at least one embodiment of the present disclosure.

FIG. 5b shows a cross-sectional view of the adapter 400 illustrating the connection between the adapter 400 and the tube 304. In some embodiments, the pump connector 306a may be, for example, a Luer-lock connector, and aperture 404 may be configured for receiving the Luer-Lock connector.

In some embodiments, the adapter 400 may be provided with sealing caps, not shown, to cover the aperture 404 and/or the septum 408. The sealing caps may be removed upon connection of the adapter 400 to the fluid delivery device 10 and/or to the tube 304.

In some embodiments, the tube 304 may be repetitively stretched and constricted to different lengths for further convenience of the subject, as demonstrated in FIGS. 6a-6b. FIG. 6a shows the tube 304 in a stretched configuration and FIG. 6b shows the tube 304 in a compact configuration. In some embodiments, the tube 304 is configured as a flexible tube enabling expansion and constriction of the tube. The tube may be configured, without limitation, as a straight tube, a spiral tube and/or a convoluted tube. In some embodiments, the tube's structure is adapted to prevent leaks and occlusions of the fluid while flowing through the tube.

Figure 7:
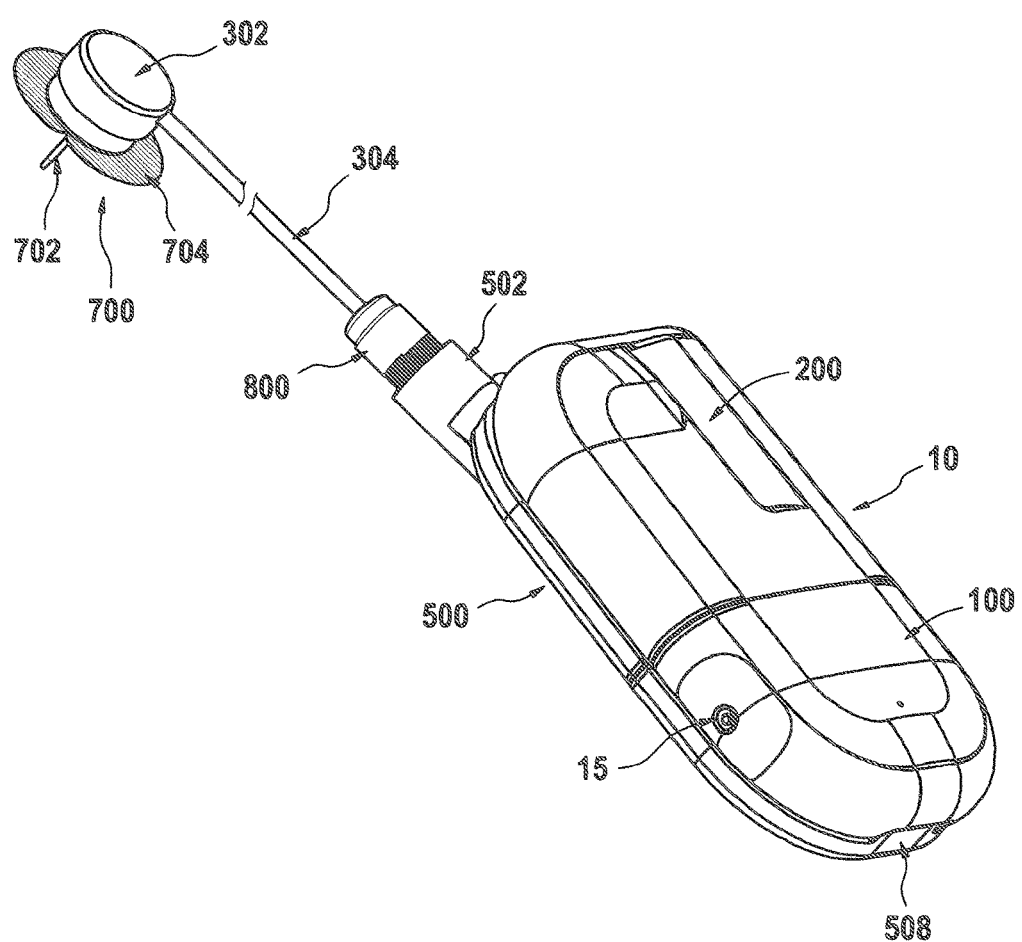
FIG. 7 illustrates the connection a of fluid delivery device to an infusion set via a cradle, according to at least one embodiment of the present disclosure.

FIG. 7 illustrates a connection of fluid delivery device 10 to an infusion set, via a cradle 500. The cradle 500 may be coupled to the fluid delivery device 10 by one or more securing mechanisms, e.g., snaps, latches, 506, 508, and may be provided with a connector configured for receiving infusion set tube 304.

In some embodiments, the connection between the cradle 500 and the tube 304 may be configured as a two-part Luer-Lock connector. For example, a channel 502, which includes a male fitting, may be provided on the cradle 500 and a female fitting 800 may be provided on the proximal end of the tube 304.

In some embodiments, the fluid delivery device 10 may be configured as a single part device or a two part device, and may include at least some of the features as described with reference to FIGS. 1a-1b.

In some embodiments, the fluid delivery device 10 may be configured for releasably connecting to a plurality of devices, for example, cradle 20, which is configured to be adhered to the body, and/or cradle 500 and/or adapter 400, which are configured to connect an infusion set. For example, the fluid delivery device 10 may be connected to adapter 400, coupled to outlet port 213, as illustrated in FIGS. 4a-c, and/or, alternatively, to cradle 20 or cradle 500 via indention 107 provided on the fluid delivery device 10.

In some embodiments, an identical infusion set, tube and/or infusion set body, may be provided to the subject, for all attachment configurations (e.g., infusion set adapter 400 and/or cradle 20, 500) of the fluid delivery device 10 to the cannula 300, 702. In other embodiments, different infusion set, tube and/or infusion set body may be provided to the subject for each attachment configurations.

In some embodiments, the infusion set may be configured as a conventional infusion set, an infusion set with detachable tube and body and/or an infusion set as described with reference to FIGS. 4-6.

In some embodiments, the female fitting 800 may be formed integrally with the tube 304. In other embodiments, the female fitting may be releasably connected to the tube 304.

Figure 8:
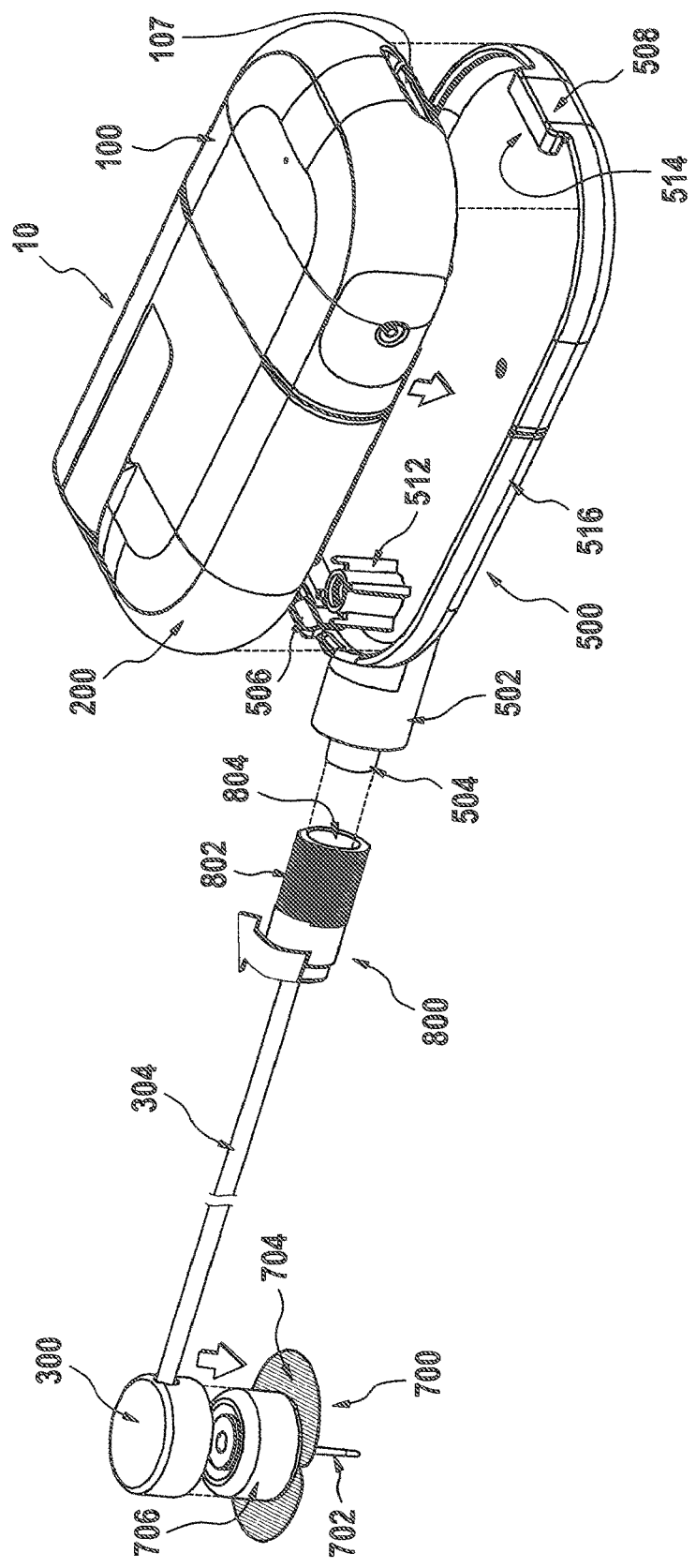
FIG. 8 illustrates a fluid delivery device, a cradle, and an infusion set, according to at least one embodiment of the present disclosure.

FIG. 8 illustrates a fluid delivery device 10, cradle 500 and an infusion set, including tube 304 and infusion set body 700, before connection.

In some embodiments, the cradle 500 may include a cradle base 514 and walls 516 configured to fit the shape of the fluid delivery device 10. The cradle 500 may be connected to the fluid delivery device 10 via one or more securing mechanisms, e.g., snaps, latches, 506, 508, configured to be received within indention 107 of the fluid delivery device 10. The cradle 500 may further include a well 512, configured to be received within the outlet port of the fluid delivery device 10, via snaps, latches etc. The well 512 may further include a self-sealable septum configured to be pierced by a connecting lumen provided in the outlet port, enabling repeated connection/disconnection of the fluid delivery device 10 to the cradle 500. When the fluid dispensing unit 10 is brought in close proximity with the well 512, the connecting lumen pierces the septum, enabling fluid communication between the reservoir (not shown) and the tube 304 via channel 502. The self-sealable septum may further prevent fluid leaking and entrance of contamination to the well 512.

In some embodiments, the cradle may be provided with a channel 502, adapted to receive the tube 304. The channel may be configured to prevent fluid occlusion or leaks. A sealing cap, which may be removed upon connection to the tube, may be provided on the channel 502, protecting the channel 502 from contamination, when not in use.

In some embodiments, the channel 502 may be configured as a male fitting of a Luer-Lock connector, which connects to a female fitting 800, provided on the proximal end of the tube 304. Upon connection of the channel 502 to the tube 304, protrusion 504, provided within channel 502, slides into a sleeve 804 of the female fitting 800, while a tabbed hub 802 of the female fitting 800 screws into threads in the inner surface of the male fitting of channel 502.

Figure 9A:
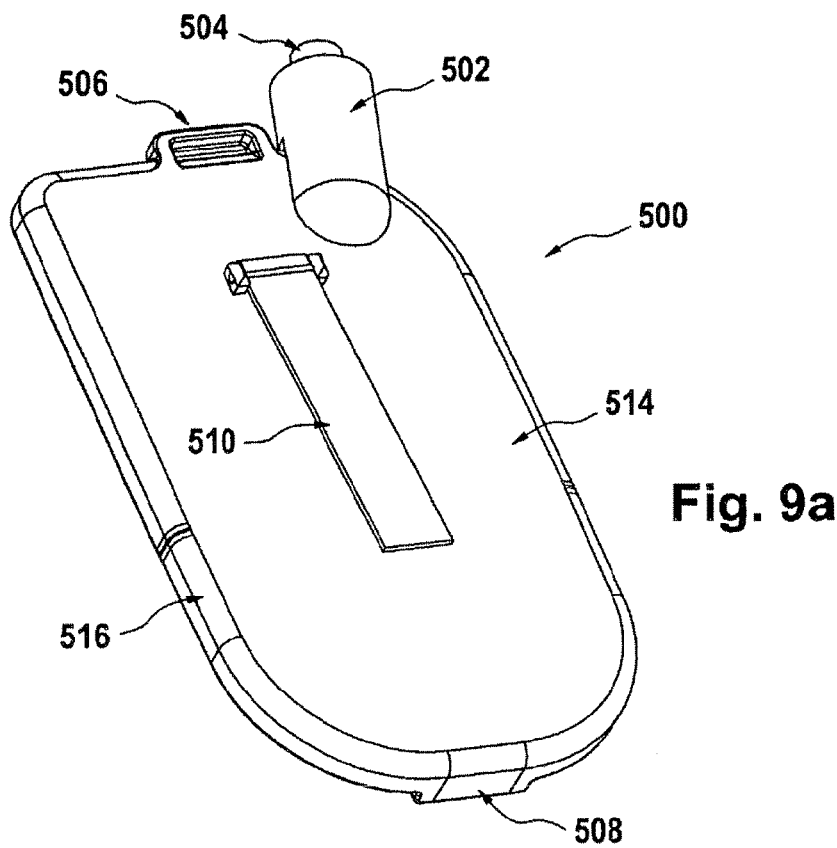
FIGS. 9a and 9b show rear and frontal views of a cradle, according to at least one embodiment of the present disclosure.
Figure 9B:
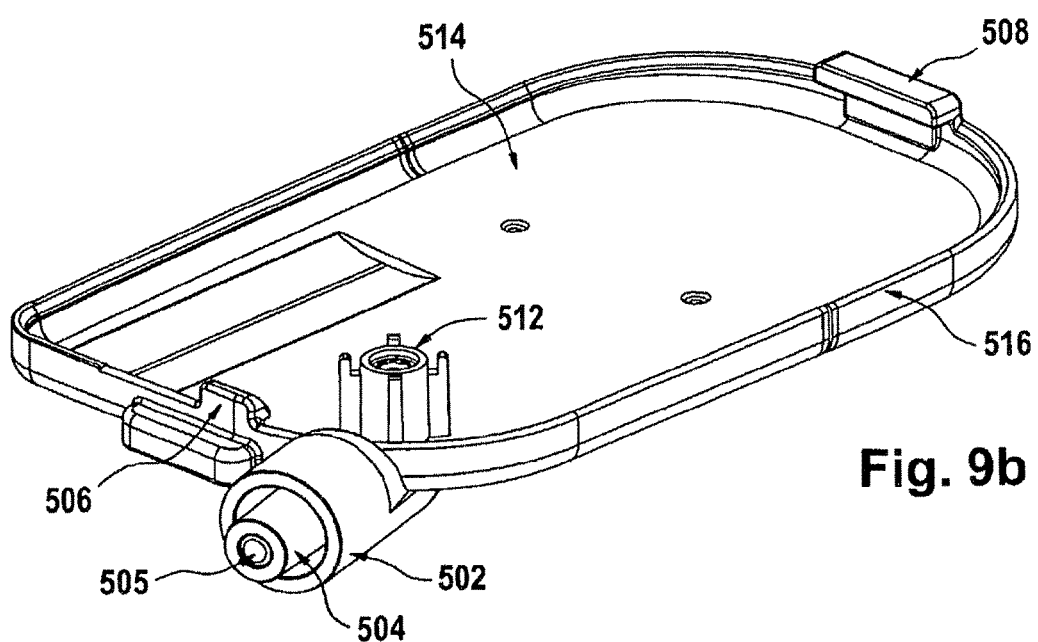

FIGS. 9a-9b show rear and frontal views of cradle 500. The cradle 500 may include means 510 for attaching the cradle 500 to the user's clothing. These means 510 may include, but are not restricted to, at least one of: a clip, a clip as shown in FIG. 9a, a magnet, a key ring, snaps with push latches, fabric hook-and-loop fasteners, and any other buckle known in the art.

Figure 10:
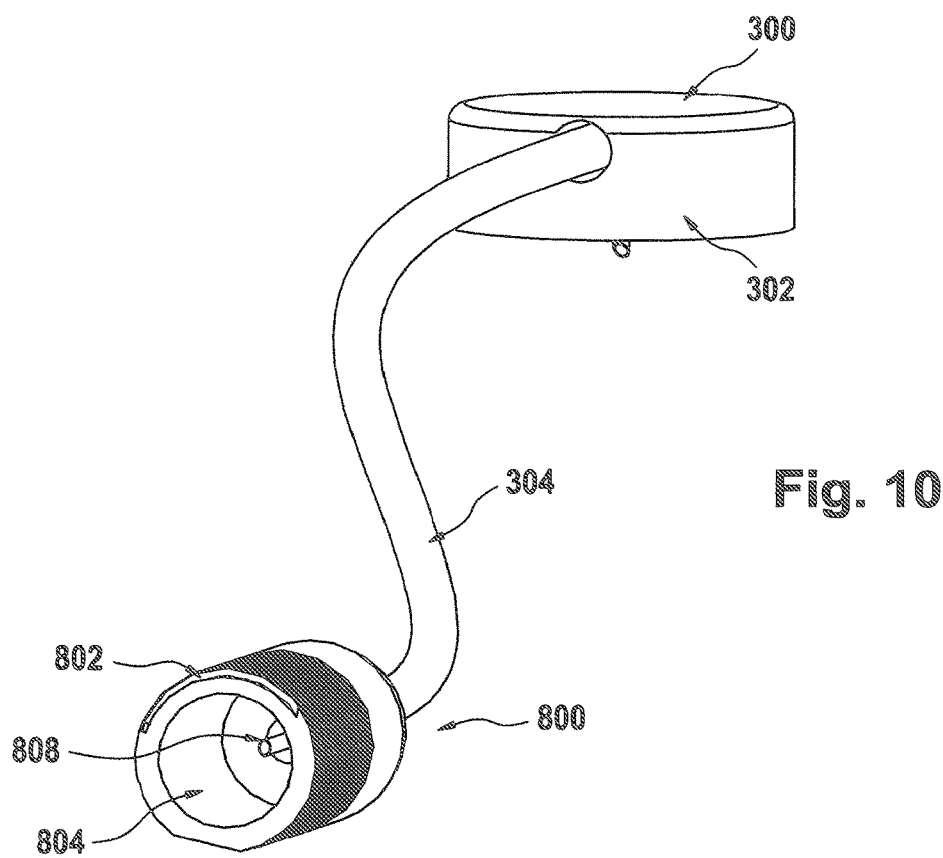
FIG. 10 illustrates a connecting lumen, according to at least one embodiment of the present disclosure.
Figure 11:
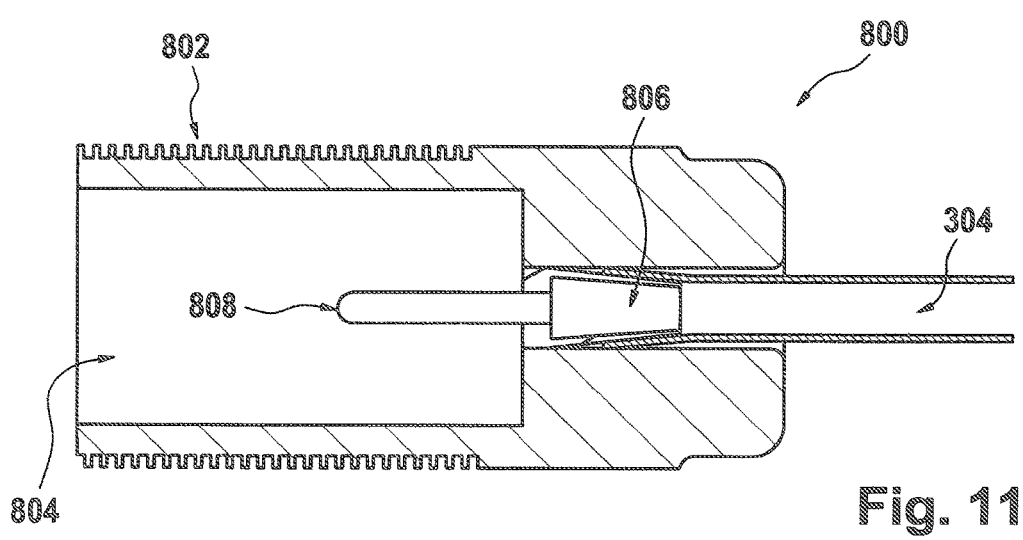
FIG. 11 shows a cut away view of the lumen illustrated in FIG. 10.

In some embodiments, the protrusion 504, within channel 502, may include a self-sealable septum 505, as shown in FIG. 9b. The self-sealable septum 505 may be configured to prevent fluid leak and contamination. The self-sealable septum 505 is further configured for being pierced, for example, by a connecting needle. A connecting lumen 808 may be provided, for example, in the female Luer-lock connecting fitting 800, located on the proximal end of the tube 304, as shown in FIGS. 10-11. The female fitting 800 may include a needle connector 806 connecting the connecting lumen 808 to the tube 304, such that the connecting lumen 808 is located within the sleeve 804. When the channel 502 is brought in close proximity with the female fitting 800, the tabbed hub 802 screws into the threads in the inner surface of the male fitting of channel 502, the protrusion 504 slides into the sleeve 804 and the connecting lumen 808 pierces the septum 505.

In some embodiments, the self-sealable septum may be provided in the female Luer-lock connecting fitting 800, and the connecting needle may be provided within the protrusion 504 of the channel 502.

The self-sealable septum and connecting needle structure within the Luer-lock connector enables repetitive connection and disconnection of the tube 304 to and from the channel 502. Furthermore, the self-sealable septum and connecting needle structure allows the tabbed hub 802 to be steadily connected to the inner surface of the male fitting of channel 502 due to friction forces or using snaps or latches.

Figure 12:
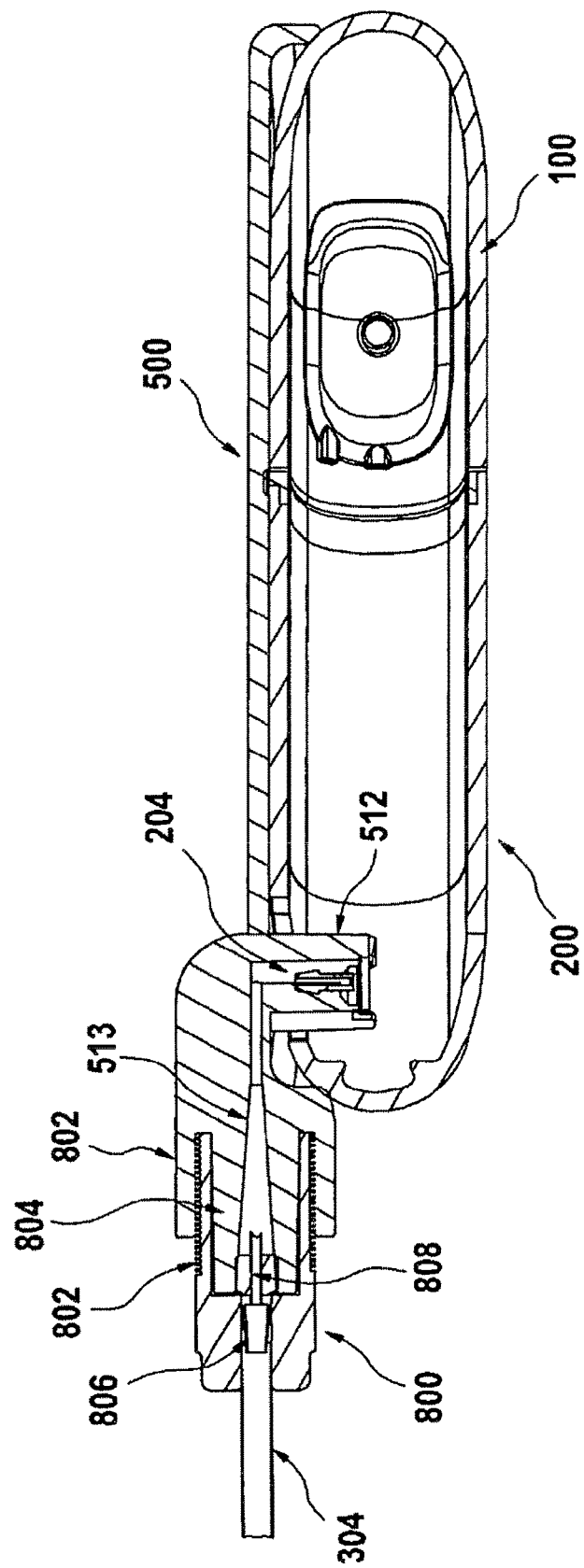
FIG. 12 is a cross-sectional view of a Luer lock connection fitting after connection of the female part to the male part, according to at least one embodiment of the present disclosure.

FIG. 12 is a cross-sectional view of the Luer-lock connecting fitting after connection of the female part 800 to the male part 502. In some embodiments, channel 502 may further include a conduit 513 which provides a fluid passageway allowing the the therapeutic fluid to flow from the outlet port of the fluid delivery device 10 to the Luer-lock connector.

Figure 13:
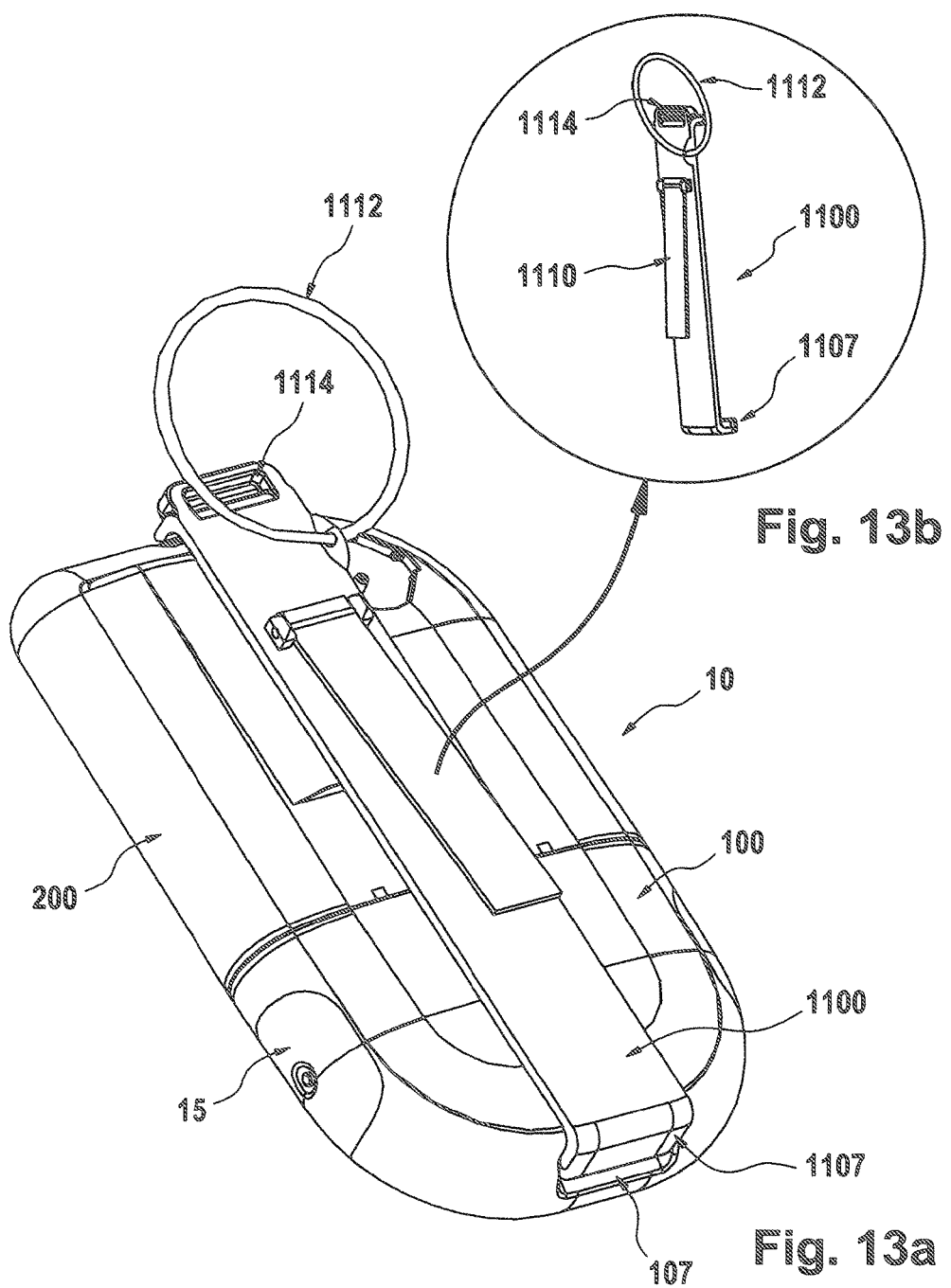
FIGS. 13a and 13b illustrate a fluid delivery device provided with a fastener, according to at least one embodiment of the present disclosure.

In some embodiment the fluid delivery device 10 may be provided with a fastener 1100, as shown in FIGS. 13a-13b. The fastener 1100 may be used to safely hold together the reusable part 100 and the disposable part 200. The fastener 1100 may include securing means (e.g., snaps, latches) 1107, configured to be received within indentation 107 of the fluid delivery device 10. The fastener 1100 may further include means for attaching the fluid delivery device to any of the user's clothing accessories. The means for attaching may include, without limitation: a clip 1110, a key ring 1112, an indentation 1114, a magnet, snaps with push latches, fabric hook-and-loop fasteners and any other detachable buckles known in the art. Any of the detachable buckles may be used for coupling the fluid delivery device to different clothing accessories, such as, for example, belt, belt loops, underwear, neck strap, sweatband, keychain, pants, etc.

Figure 14:
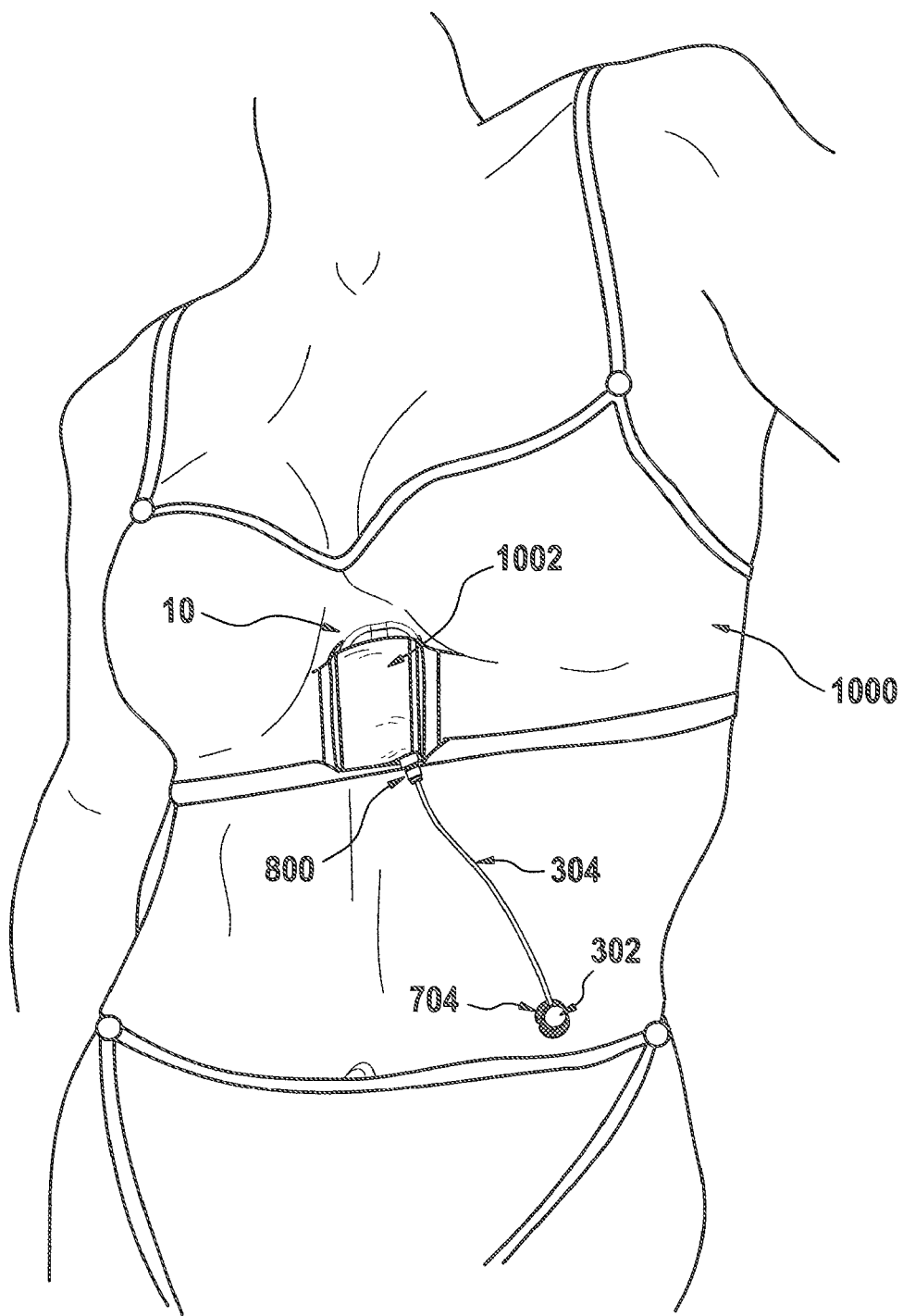
FIG. 14 illustrates an undergarment carrying device for a fluid delivery device, according to at least one embodiment of the present disclosure.
Figure 15:
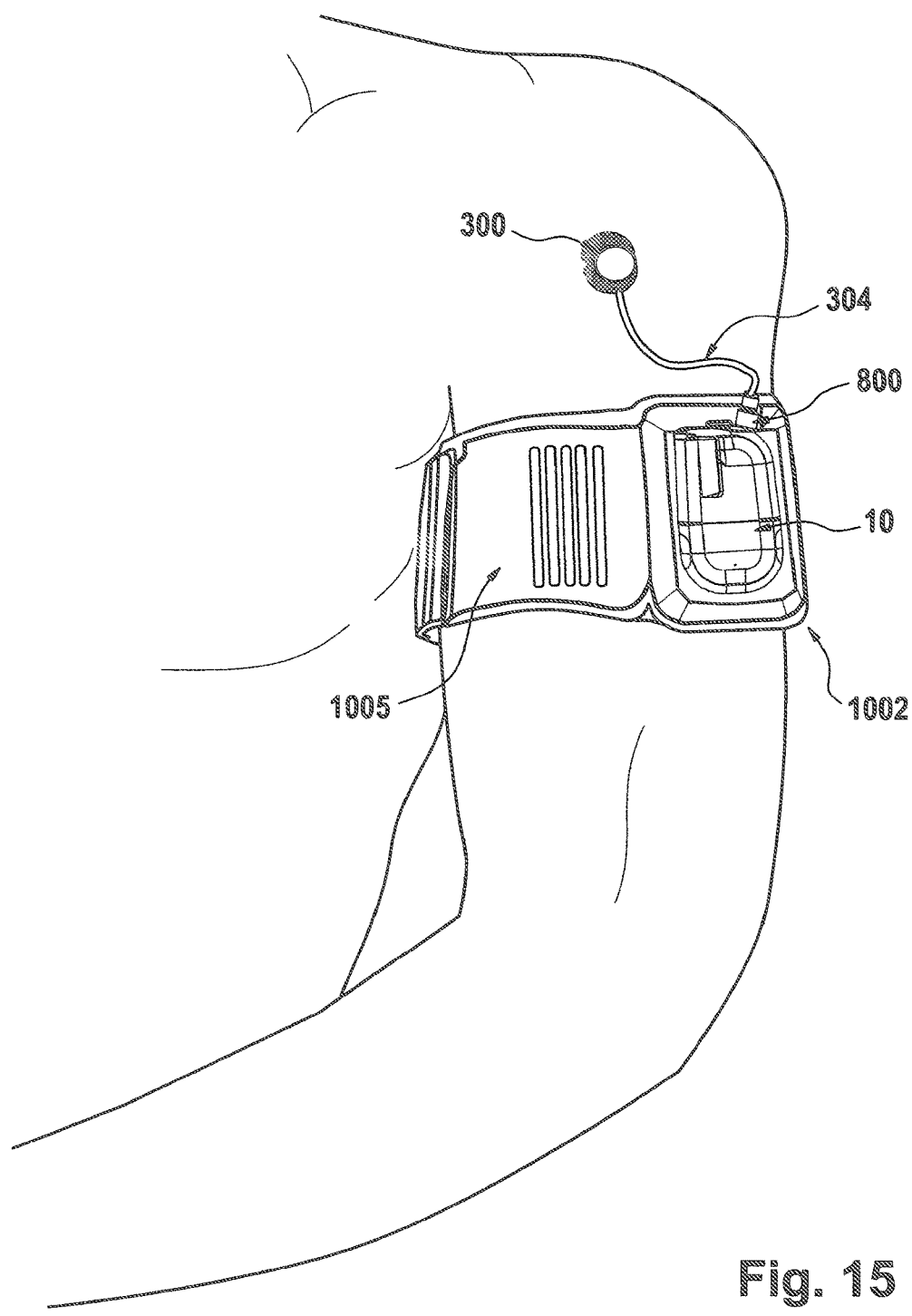
FIG. 15 illustrates an arm band carrying device for a fluid delivery device, according to at least one embodiment of the present disclosure.

FIGS. 14-15 show some examples of carrying the fluid delivery device 10 using a case 1002. The case 1002 may be made of fabric, leather, synthetic leather, plastic, etc. In some embodiments, the case 1002 may include an opening for inserting the fluid delivery device 10. In some embodiments, the case 1002 may further include a second opening allowing access for connecting the tube 304, using connector 800, for example. The case 1002 may be attached to any clothing accessories, including, but not limited to: underwear, bra, belt, belt loops, pouch, band, sweatband, neck strap, pants and any other accessories known it the art. FIG. 14 illustrates an example of coupling the case 1002 to a woman's bra 1000. This location is discreet and provides comfortable access to the fluid delivery device 10. FIG. 15 illustrates an example of coupling the case 1002 to a band 1005. The band 1005 may be placed on the subject's arm (as shown), wrist, thigh, shin or waist. In some embodiments, the band 1005 may be configured for stretching and constricting in order to be wrapped around different body parts, using Velcro, belt buckle, fabrication from elastic materials, etc. In some embodiments, the case 1002 may be coupled to a neck strap, such that the case 1002 with the fluid delivery device 10 may lay on the body, below the blouse, in a concealed manner, while allowing comfortable access of the user to the fluid delivery device 10. In some embodiments, the case 1002 may be attached to the clothing accessory permanently by sewing or gluing for example. In other embodiments, the case may include means for temporary attachment to the clothing accessory, for example: a clip, a magnet, a key ring, snaps with push latches, fabric hook-and-loop fasteners, safety pin, snap fastener, zipper, buttons, button loop, Hook-and-eye closure, etc. A temporary attachment may allow the subject to change the patch placement to different sites during a period of time, while the delivery of the fluid is uninterrupted.

Figure 16:
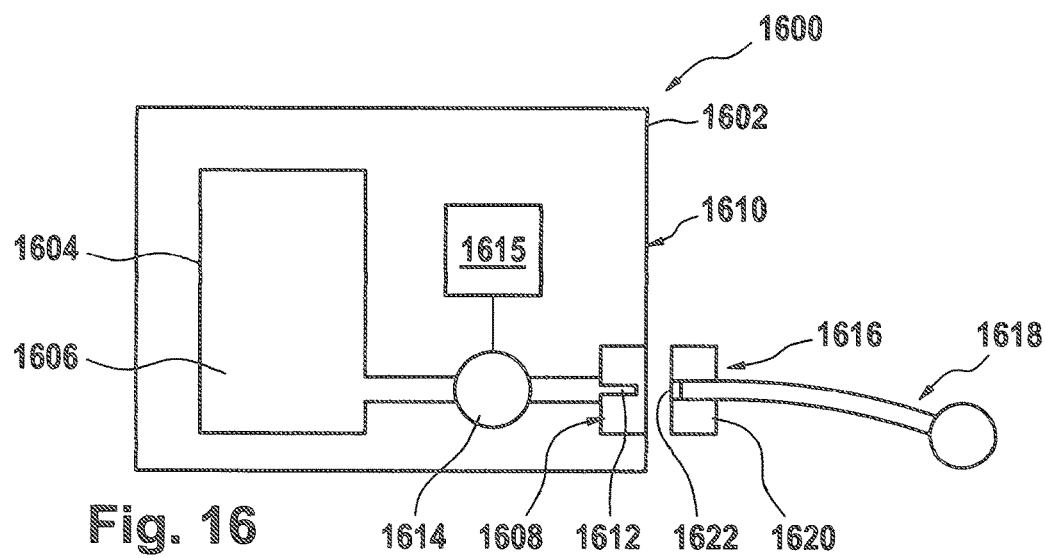
FIG. 16 shows a therapeutic device, according to at least one embodiment of the present disclosure.

FIG. 16 shows a therapeutic device 1600 according to at least one embodiment of the present disclosure. The therapeutic device 1600 comprises a fluid delivery device 1602. The fluid delivery device 1602 comprises a fluid reservoir 1604 filled with a fluid 1606. There is an outlet port 1608 on an exterior surface 1610 of the fluid delivery device 1602. Within the outlet port 1608 there is a lumen 1612 for which the fluid 1606 can be pumped out by a pump 1614. The pump 1614 is controlled by a controller 1615. There is an adaptor 1616 for an infusion set 1618. The adaptor 1616 comprises a plug 1620 which is adapted for connecting to the outlet port 1608. The plug 1620 comprises an adaptor septum 1622 which is operable for being pierced by the lumen 1612.

Figure 17:
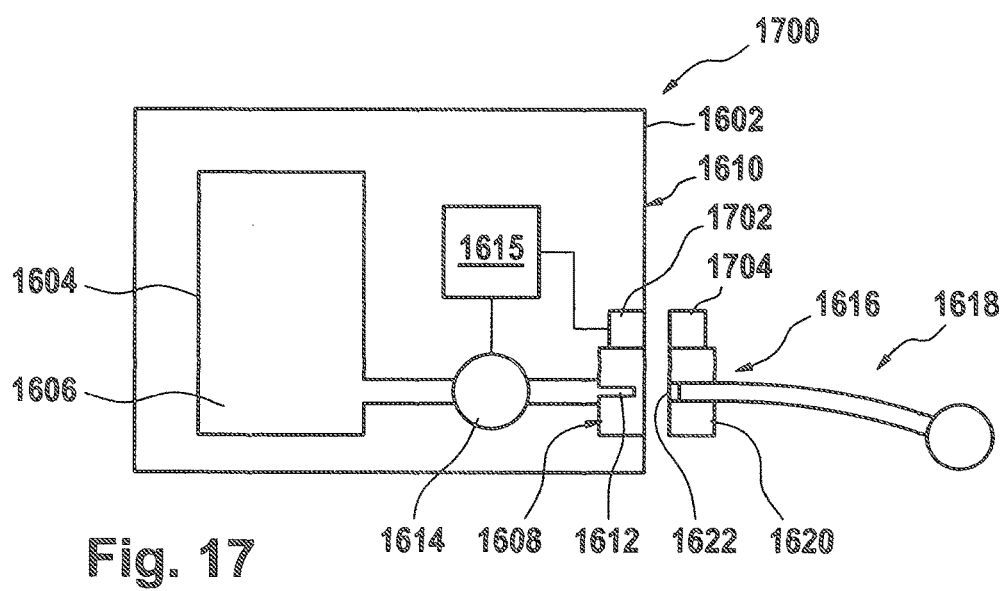
FIG. 17 shows a therapeutic device, according to at least one embodiment of the present disclosure.

FIG. 17 illustrates a therapeutic device 1700 according to a further embodiment of the present disclosure. The embodiment shown in FIG. 17 is similar to that shown in FIG. 16. In the embodiment shown in FIG. 17 there is additionally an infusion set recognition system 1702 that is a component of the fluid delivery device 1602. The infusion set recognition system 1702 is connected to the controller 1615. The controller is able to query the infusion set recognition system for infusion set data. Infusion set data as used herein encompasses data which is descriptive of the infusion set 1618. The infusion set recognition system 1702 may be based on one or more of different types of systems. The recognition system 1702 may incorporate an RFID system, a barcode reader, a hologram recognition system, and an electronic plug incorporated into the outlet port 1608. The recognition token 1704 depends upon the type of infusion set recognition system 1702. The infusion set token 1704 may also be located on the infusion set 1618 instead of the plug 1616. For instance in the case of an RFID infusion set recognition system the RFID tag 1704 may be incorporated directly into the infusion set 1618.

Figure 18:
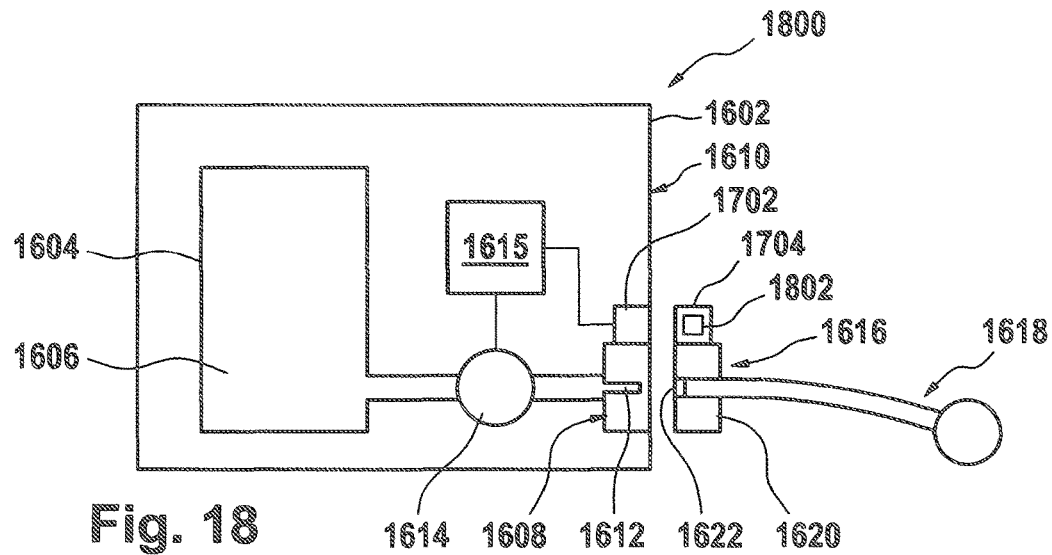
FIG. 18 shows a therapeutic device, according to at least one embodiment of the present disclosure.

FIG. 18 illustrates a further embodiment of a therapeutic device according to the present disclosure. The embodiment shown in FIG. 18 is similar to that shown in FIG. 17. However, in this case the recognition token 1704 has a memory 1802. In this case the memory 1802 may be read or written to by the infusion set recognition system 1702. The memory 1802 may be considered to be an information carrier for storing the infusion set data. The memory 1802 may be used to record such things as the usage of the infusion set as well as details about the infusion set 1618 or even instructions which allow the processor 1615 to properly control the pump 1614 for using the infusion set 1618.

Figure 19:
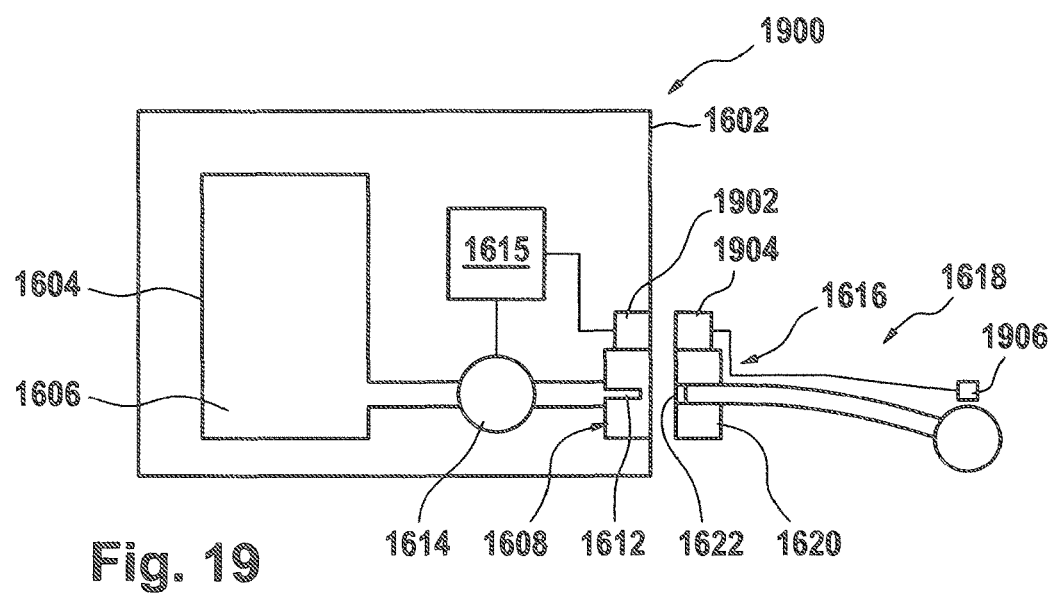
FIG. 19 shows a therapeutic device, according to at least one embodiment of the present disclosure.

FIG. 19 illustrates a further embodiment of a therapeutic system 1900 according to an embodiment of the present disclosure. In this embodiment the processor 1615 has a controller sensor connector 1902. The controller sensor connector 1902 is adapted for connecting to a sensor adaptor 1904. The sensor adaptor 1904 enables the processor 1615 to communicate with a sensor 1906. The sensor 1906 may represent one or more sensors which may be used for measuring a physical property of a subject and/or monitoring the state of fluid 1606 being pumping through the infusion set 1618. For instance the sensor 1906 may be a flow or occlusion sensor for monitoring the fluid 1606. In other embodiments the sensor 1906 may also be such things as a glucose sensor for measuring blood glucose.

The sensor 1906 may also be connected to the controller 1615 in other ways. For instance the sensor adaptor 1904 may be a wireless or RFID compatible system and the controller sensor connector 1902 may be replaced with an equivalent such as an RFID reader or wireless communication reader.

Figure 20:
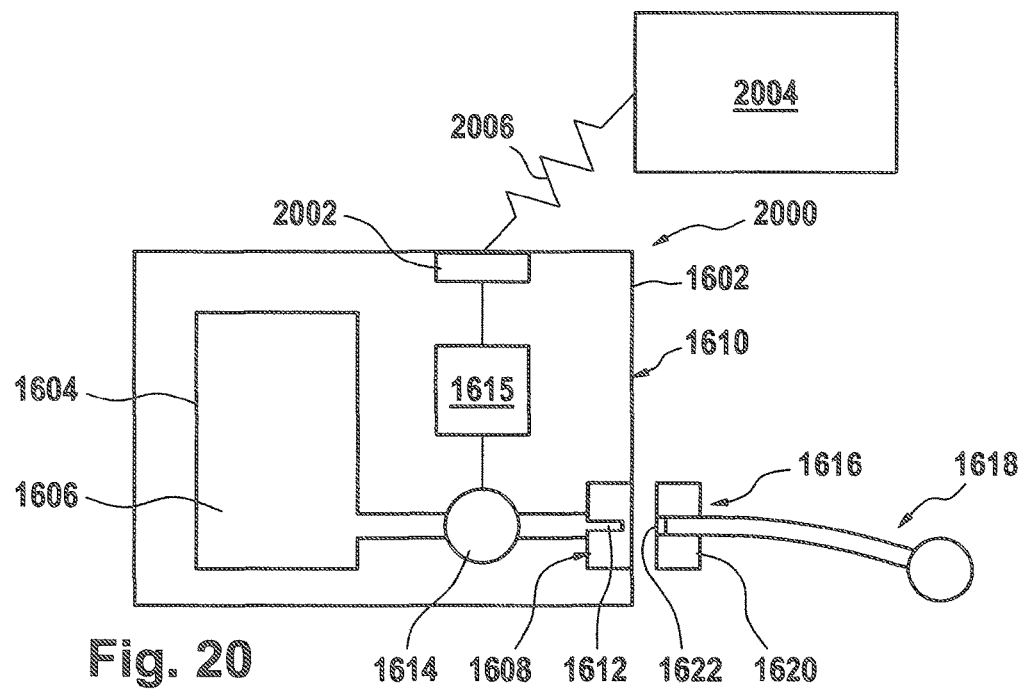
FIG. 20 shows a therapeutic device, according to at least one embodiment of the present disclosure.

FIG. 20 illustrates a therapeutic device 2000 according to a further embodiment of the present disclosure. In this embodiment there is a network adaptor 2002 connected to the controller 1615. This enables the controller 1615 to form a communications channel 2006 for communicating with a computer system or a network. This may enable the controller 1615 to send such things as details about the pumping of fluid 1606 through the infusion set 1618 when combined with the embodiment shown in FIG. 17, 18 or 19, various sensor data and/or specific data about the infusion sets used may also be communicated to the computer system or network 2004. The network adaptor 2002 and the communications channel 2006 are intended to be representative and may represent any number of typical wireless or wired communications protocol and appropriate hardware.

Figure 21:
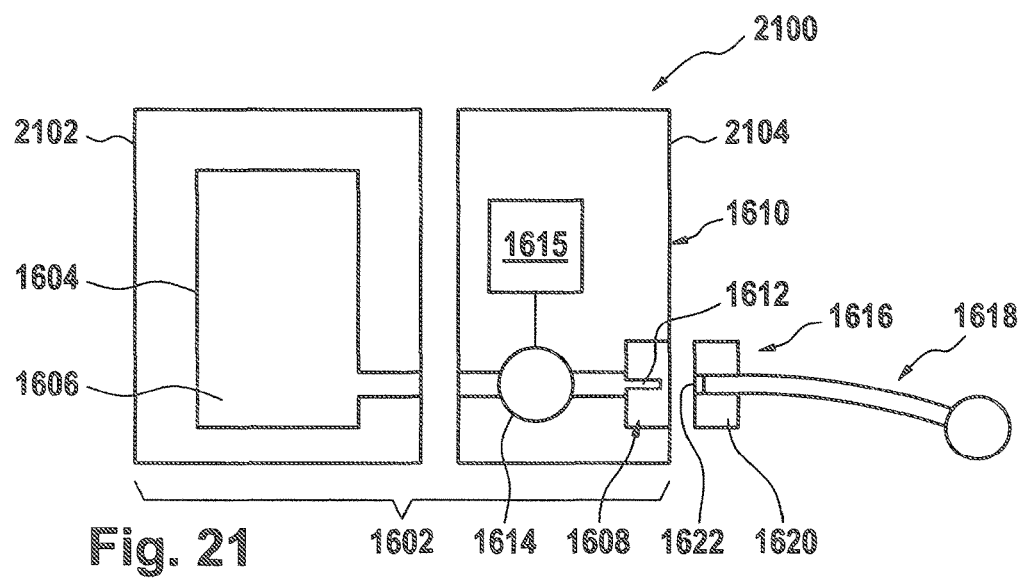
FIG. 21 shows a therapeutic device, according to at least one embodiment of the present disclosure.

FIG. 21 shows an embodiment of a therapeutic device according to at least one embodiment of the present disclosure. The embodiment shown in FIG. 21 is similar to that shown in FIG. 16. However in this case the fluid delivery device 1602 is divided into a disposable portion 2102 and a reusable portion 2104. This embodiment may enable the reservoir 1604 to be replaced when the fluid is run out or becomes too old to use. The embodiments shown in FIGS. 16, 17, 18, 19, 20, and 21 may have their features combined.

Embodiments of the present disclosure may have one or more of the following features and/or advantages.

1. Due to the use of a cradle/base in a patch pump, the adapter may provide the ability to use the patch pump both with the cradle/base and the infusion set, interchangeably, allowing the user to enjoy the advantages of both of them by replacing them according to his/hers need.

2. Replacement between the cradle/base and the infusion set "modes" can be done without losing and/or wasting any amount of drug, such as insulin, because the same reservoir and/or DP is used.

3. More insertion sites are available to the user due to the relatively small adhesion area of the infusion set in comparison to a normal patch pump.

4. In some configurations, the same cannula unit is used both with the cradle and the infusion set, so the user would not have to prick himself and/or herself over and over again every time he/she wishes to replace between the body connection means and/or "modes" such as a cradle and/or base and an infusion set.

5. Since the patch device is small and light, when used with an infusion set, it is not limited to be secured to a belt, as conventional "pager-like" devices do.

Embodiments described herein may be secured to any of the user's clothes and accessories by introducing attaching means to the device. Attaching means can be, for example: a clip, which can be attached for example to underwear or a key ring and an indentation with a strap, for example which can be wrapped around the neck and placed below the clothes or wrapped around the arm. Of course, other detachable buckles, cases, etc., can also be used.

6. An additional advantage relates to the tube of the infusion set: the infusion set can include a tube which is capable of being repetitively stretched and constricted, to several different lengths. This feature provides further convenience to the subject.

The invention claimed is:

1. A therapeutic system comprising:
a fluid delivery device, wherein the fluid delivery device comprises:
a fluid reservoir for storing a fluid;
an outlet port with a lumen for outputting the fluid from the reservoir, wherein the outlet port is formed on an exterior surface of the fluid delivery device;
a pump for pumping the fluid through the lumen;
a controller for controlling the therapeutic system, wherein the controller is operable for regulating the pumping of fluid through the lumen;
an adaptor for an infusion set, wherein the adaptor comprises a plug operable for attaching to the outlet port, and wherein the adaptor comprises an adaptor septum operable for being pierced by the lumen when attached to the outlet port;
an infusion set recognition system, wherein the controller is further operable to query the infusion set recognition system for infusion set data, wherein the infusion set data comprises an infusion set type, wherein the controller is further operable to operate the pump to provide a basal dosage of the fluid if the infusion set type is not recognized;
a tube port which comprises a tube port lumen;
a tube with a first end and a second end, wherein the first end is connected to the adaptor and the second end is connected to the tube port; and
a hub operable for attaching to the tube port, wherein the hub comprises a hub cannula, a hub cannula septum, and an adhesive layer for attaching to an outer surface of a subject, wherein the hub cannula septum is operable for being pierced by the tube port lumen when the hub is attached to the tube port, and wherein the hub is further operable for attaching to the outlet port, wherein the hub cannula septum is operable for being pierced by the lumen.

2. The therapeutic system of claim 1, wherein the infusion set recognition system is one of an RFID system, a bar code reader, a hologram recognition system, an electronic plug incorporated into the outlet port, a mechanical coupling arrangement or a combination thereof.

3. The therapeutic system of claim 1, wherein the therapeutic system further comprises the infusion set, wherein the infusion set further comprises an information carrier for storing the infusion set data, wherein the infusion set recognition system is adapted for retrieving the infusion set data from the information carrier by querying the infusion set.

4. The therapeutic system of claim 3, wherein the infusion set data comprises any one of the following: sterility state, therapeutic system compatibility data or code, approved use data or code, lot number, batch number, hose diameter, manufacturer, approved therapy data or code, and combinations thereof.

5. The therapeutic system of claim 3, wherein the infusion set recognition system is further operable for writing usage data to the information carrier, wherein the usage data comprises any one of the following: prior use and cumulative use, wherein the infusion set adaptor is further operable to query previously written usage data.

6. The therapeutic system of claim 5, wherein the controller is operable to disable and/or display a warning on a display in accordance with the previously written usage data.

7. The therapeutic system of claim 1, wherein the controller comprises a memory, wherein the controller is operable for recording utilization data of the infusion set and the infusion set data in the memory.

8. The therapeutic system of claim 7, wherein the therapeutic system is operable for sending the utilization data and the infusion set data to a computer system.

9. The therapeutic system of claim 1, wherein the infusion set data further comprises a software update, and wherein the controller is operable for controlling the operation of the pump in accordance with the software update.

10. The therapeutic system of claim 1, wherein the therapeutic system further comprises a cradle for supporting the fluid delivery device, wherein the cradle and the fluid delivery device are operable for forming an interlocking connection for removably affixing the fluid delivery device to the cradle, wherein the cradle comprises an adhesive layer for attaching to the outer surface of a subject, wherein the cradle further comprises a passageway operable for attaching to the outlet port and for receiving a cannula with a cannula septum operable for being pierced by the lumen when attached to the outlet port.

11. The therapeutic system of claim 1, wherein the adaptor further comprises a tube mount operable for mounting to an infusion set tube.

12. The therapeutic system of claim 1, wherein the therapeutic system further comprises the infusion set attached to the adaptor.

13. The therapeutic system of claim 1, wherein the tube is any one of the following: is spiral shaped, is contained within a spring loaded spool, has a convoluted shape, and is attached to an elastic strap.

14. The therapeutic system of claim 1, wherein the outlet port further comprises a first electrical connector, and wherein the adaptor further comprises a second electrical connector operable for forming an electrical connection with the first electrical connector for transmitting a sensor signal to the processor.

15. The therapeutic system of claim 1, wherein the therapeutic system further comprises the infusion set, wherein the infusion set comprises a sensor.

16. The therapeutic system of claim 15, wherein the sensor is an occlusion sensor or a flow sensor, wherein the controller is further operable to: receive the sensor signal from the sensor; detect an occlusion condition using the sensor signal; and generate a warning message if the occlusion condition is detected.

17. The therapeutic system of claim 15, wherein the sensor is a subcutaneous sensor; wherein the controller is further operable to receive the sensor signal; wherein the controller is further operable to perform any one of the following: log the sensor signal; and adjust the pumping of fluid through the lumen in accordance with the sensor signal.

18. The therapeutic system of claim 1, wherein the therapeutic system further comprises a network adaptor for communicating with a computer, wherein the controller is further operable to identify an alert condition and send an alert notification message to the computer using the network adaptor.

19. The therapeutic system of claim 1, wherein the fluid delivery device comprises a reusable portion and a disposable portion, wherein the reusable portion comprises: the pump, a memory, and a processor; and wherein the disposable portion comprises the fluid reservoir.

20. The therapeutic system of claim 1, wherein the therapeutic system further comprises a support garment operable for supporting the fluid delivery device.

21. The therapeutic system of claim 1, wherein the fluid delivery system is an insulin pump.

22. A therapeutic system comprising:
a fluid delivery device, wherein the fluid delivery device comprises:
   a fluid reservoir for storing a fluid;
   an outlet port with a lumen for outputting the fluid from the reservoir, wherein the outlet port is formed on an exterior surface of the fluid delivery device;
   a pump for pumping the fluid through the lumen;
   a controller for controlling the therapeutic system, wherein the controller is operable for regulating the pumping of fluid through the lumen;
an adaptor for an infusion set, wherein the adaptor comprises a plug operable for attaching to the outlet port, and wherein the adaptor comprises an adaptor septum operable for being pierced by the lumen when attached to the outlet port;
wherein the adaptor is operable for supporting the fluid delivery device, wherein the adaptor and the fluid delivery device are operable for forming an interlocking connection for removably affixing the fluid delivery device to the adaptor;
wherein the adaptor comprises a tube mount operable for mounting a tube of the infusion set, wherein the tube mount has a first axis, wherein the plug has a second axis, wherein when the first axis and the second axis are projected onto a plane through the first axis the first axis and the second axis form an angle between 30 and 150 degrees,
wherein the tube has a first end and a second end, wherein the first end is connected to the adaptor via the tube mount and the second end is connected to a tube port, wherein the tube port comprises a tube port lumen; and
a hub operable for attaching to the tube port, wherein the hub comprises an adhesive layer for attaching to an outer surface of a subject, wherein the hub comprises a hub cannula and a hub cannula septum, wherein the hub cannula septum is operable for being pierced by the tube port lumen when the hub is attached to the tube port, and wherein the hub is further operable for attaching to the outlet port, wherein the hub cannula septum is operable for being pierced by the lumen.

23. The therapeutic system of claim 22, wherein the tube mount is a Luer-lock.

24. A kit comprising:
a fluid delivery device, wherein the fluid delivery device comprises:
   a fluid reservoir for storing a fluid;
   an outlet port with a lumen for outputting the fluid, wherein the outlet port is formed on an exterior surface of the fluid delivery device;
   a pump for pumping the fluid through the lumen;
   a controller for controlling the therapeutic system, wherein the controller is operable to regulate the pumping of fluid through the lumen;
an adaptor for an infusion set, wherein the adaptor comprises a plug operable for attaching to the outlet port, wherein the outlet port comprises an adaptor septum operable for being pierced by the lumen;
a cradle for supporting the fluid delivery device, wherein the cradle and the fluid delivery device are operable for forming an interlocking connection for removably affixing the fluid delivery device to the cradle, wherein the cradle comprises an adhesive layer for attaching to an outer surface of a subject, wherein the cradle further comprises a passageway operable for attaching to the outlet port and for receiving a cannula with a cannula septum operable for being pierced by the lumen, wherein the kit enables the user to operate the fluid delivery device mounted on the outer surface of the subject or in an a remote mode where the fluid delivery device is connected to the infusion set;
a tube with a first end and a second end, wherein the first end is connected to the adaptor, where the second end is connected to a tube port, wherein the tube port comprises a tube port lumen; and
a hub operable for attaching to the tube port, wherein the hub comprises an adhesive layer for attaching to an outer surface of a subject, wherein the hub comprises a hub cannula and a hub cannula septum, wherein the hub cannula septum is operable for being pierced by the tube port lumen when the hub is attached to the tube port, and wherein the hub is further operable for attaching to the outlet port, wherein the hub cannula septum is operable for being pierced by the lumen.

* * * * *